US012569311B2

(12) United States Patent
Schneider et al.

(10) Patent No.: US 12,569,311 B2
(45) Date of Patent: Mar. 10, 2026

(54) FIBER OPTIC SHAPE SENSING MANAGEMENT

(71) Applicant: Northern Digital Inc., Waterloo (CA)

(72) Inventors: Mark Robert Schneider, Williston, VT (US); Jose Luis Alarcon Herrera, Waterloo (CA); Utsav Pardasani, Waterloo (CA)

(73) Assignee: Northern Digital Inc., Waterloo (CA)

( * ) Notice: Subject to any disclaimer, the term of this patent is extended or adjusted under 35 U.S.C. 154(b) by 120 days.

(21) Appl. No.: 18/664,655

(22) Filed: May 15, 2024

(65) Prior Publication Data

US 2024/0382129 A1     Nov. 21, 2024

Related U.S. Application Data

(60) Provisional application No. 63/502,240, filed on May 15, 2023.

(51) Int. Cl.
A61B 90/00          (2016.01)
A61B 5/06           (2006.01)
         (Continued)

(52) U.S. Cl.
CPC .............. A61B 90/06 (2016.02); A61B 5/062 (2013.01); A61B 34/20 (2016.02); G01B 11/00 (2013.01);
         (Continued)

(58) Field of Classification Search
CPC ........... A61B 90/06; A61B 5/62; A61B 34/20; A61B 2034/2061; A61B 2090/064;
         (Continued)

(56) References Cited

U.S. PATENT DOCUMENTS 4,951,674 A * 8/1990 Zanakis ................. A61B 5/248
                                                     600/409
5,377,678 A    1/1995 Dumoulin et al.
         (Continued)

FOREIGN PATENT DOCUMENTS

CA        2324894        4/2001
JP        S6184571 A  *  4/1986

OTHER PUBLICATIONS

Jäckle et al., "Fiber optical shape sensing of flexible instruments for endovascular navigation," CoRR, Submitted on Jun. 25, 2019, arXiv:1908.02120, 12 pages.
         (Continued)

*Primary Examiner* — Jennifer D Bennett
(74) *Attorney, Agent, or Firm* — Fish & Richardson P.C.

(57)          ABSTRACT

Methods, systems, and apparatus, including computer programs encoded on computer storage media, for tracking fiber optic shaping. In some implementations, a server obtains optical signals reflected through a fiber, the fiber comprising one or more embedded sensors and a nano-magnetometer embedded at a distal location of the fiber. The server determines a frequency shift of each of the reflected optical signals, the frequency shift imparted on the reflected optical signals by the one or more embedded sensors. The server determines a phase shift of each of the reflected optical signals, the phase shift imparted on the reflected optical signals by the nano-magnetometer. The server determines characteristics of the fiber using the determined frequency and the phase shift of each of the reflected optical signals, the characteristics comprises a shape of the fiber and a location of the fiber in relation to an external reference.

30 Claims, 11 Drawing Sheets

(51) Int. Cl.

| | |
|---|---|
| *A61B 34/20* | (2016.01) |
| *G01B 11/00* | (2006.01) |
| *G01B 11/24* | (2006.01) |

(52) U.S. Cl.

CPC ...... *G01B 11/24* (2013.01); *A61B 2034/2061* (2016.02); *A61B 2090/064* (2016.02); *A61B 2562/0223* (2013.01); *A61B 2562/0266* (2013.01); *A61B 2562/0285* (2013.01)

(58) Field of Classification Search

CPC .... A61B 2562/0223; A61B 2562/0266; A61B 2562/0285; G01B 11/00; G01B 11/24

See application file for complete search history.

(56) References Cited

U.S. PATENT DOCUMENTS

| | | | |
|---|---|---|---|
| 6,545,760 B1 | 4/2003 | Froggatt et al. | |
| 7,742,799 B2 | 6/2010 | Mueller et al. | |
| 7,772,541 B2 | 8/2010 | Froggatt et al. | |
| 7,781,724 B2 | 8/2010 | Childers et al. | |
| 7,813,599 B2 | 10/2010 | Moore | |
| 8,123,400 B2 | 2/2012 | Andrejco et al. | |
| 8,183,520 B2 | 5/2012 | Prisco | |
| 8,276,462 B2 | 10/2012 | Tao et al. | |
| 8,515,215 B2 | 8/2013 | Younge et al. | |
| 8,520,986 B2 | 8/2013 | Dailey | |
| 8,746,076 B2 | 6/2014 | Rogge et al. | |
| 8,773,650 B2 | 7/2014 | Froggatt et al. | |
| 8,970,845 B1 | 3/2015 | Chen et al. | |
| 9,200,971 B2 | 12/2015 | Froggatt et al. | |
| 9,417,057 B2 | 8/2016 | Hooft et al. | |
| 9,423,311 B2 | 8/2016 | Moslehi | |
| 9,441,954 B2 | 9/2016 | Ramamurthy et al. | |
| 9,494,809 B2 | 11/2016 | Yamada et al. | |
| 9,693,707 B2 | 7/2017 | Chan et al. | |
| 9,733,336 B2 | 8/2017 | Shen et al. | |
| 9,757,034 B2 | 9/2017 | Desjardins et al. | |
| 9,784,569 B2 | 10/2017 | Froggatt et al. | |
| 9,841,269 B2 | 12/2017 | Froggatt et al. | |
| 9,861,271 B2 | 1/2018 | Liu et al. | |
| 9,918,659 B2 | 3/2018 | Chopra et al. | |
| 9,958,605 B2 | 5/2018 | Wei et al. | |
| 10,178,945 B2 | 1/2019 | Kuboi et al. | |
| 10,317,196 B2 | 6/2019 | Laine et al. | |
| 10,376,321 B2 | 8/2019 | DiMaio et al. | |
| 10,378,883 B2 | 8/2019 | Gifford et al. | |
| 10,422,631 B2 | 9/2019 | Reaves et al. | |
| 10,531,828 B2 | 1/2020 | Bell et al. | |
| 10,551,170 B2 | 2/2020 | Hooft et al. | |
| 10,610,306 B2 | 4/2020 | Chopra et al. | |
| 10,612,911 B1 | 4/2020 | Pena, III et al. | |
| 10,663,290 B1 | 5/2020 | Tongue et al. | |
| 10,775,157 B2 | 9/2020 | Gifford et al. | |
| 10,859,411 B2 | 12/2020 | Alemohammad et al. | |
| 10,869,603 B2 | 12/2020 | Millett et al. | |
| 10,905,855 B2 | 2/2021 | Leo | |
| 11,007,027 B2 | 5/2021 | Fuerst et al. | |
| 11,035,699 B2 | 6/2021 | Froggatt et al. | |
| 11,079,217 B2 | 8/2021 | Van Putten et al. | |
| 11,173,597 B2 | 11/2021 | Rabindran et al. | |
| 11,353,524 B1 | 6/2022 | Strutner et al. | |
| 2004/0152970 A1 | 8/2004 | Hunter et al. | |
| 2005/0187463 A1 | 8/2005 | Quistgaard et al. | |
| 2006/0082789 A1 | 4/2006 | Goldbach | |
| 2006/0103380 A1* | 5/2006 | Kochergin | G01R 33/0322 |
| | | | 324/244.1 |
| 2010/0030063 A1 | 2/2010 | Lee et al. | |
| 2010/0317964 A1 | 12/2010 | Hendriks et al. | |
| 2012/0001625 A1* | 1/2012 | Yamada | G02F 1/0036 |
| | | | 324/244.1 |
| 2013/0102878 A1 | 4/2013 | Burg et al. | |
| 2013/0131503 A1 | 5/2013 | Schneider et al. | |
| 2014/0070802 A1 | 3/2014 | Yamada et al. | |
| 2016/0370177 A1 | 12/2016 | Laine et al. | |

| | | | |
|---|---|---|---|
| 2017/0238996 A1 | 8/2017 | Frame et al. | |
| 2017/0325895 A1 | 11/2017 | Krimsky | |
| 2018/0256262 A1 | 9/2018 | Duindam et al. | |
| 2018/0289927 A1 | 10/2018 | Messerly | |
| 2019/0000562 A1 | 1/2019 | Thienphrapa et al. | |
| 2019/0143506 A1 | 5/2019 | Rabindran et al. | |
| 2019/0234726 A1 | 8/2019 | Gifford et al. | |
| 2019/0307995 A1 | 10/2019 | Flexman et al. | |
| 2019/0390985 A1 | 12/2019 | Kwok et al. | |
| 2020/0188036 A1 | 6/2020 | Ding et al. | |
| 2020/0188038 A1 | 6/2020 | Donhowe et al. | |
| 2020/0214598 A1 | 7/2020 | Li et al. | |
| 2020/0264018 A1 | 8/2020 | Froggatt et al. | |
| 2021/0038322 A1 | 2/2021 | Thompson et al. | |
| 2021/0045814 A1 | 2/2021 | Thompson et al. | |
| 2021/0116265 A1 | 4/2021 | Takakuma et al. | |
| 2021/0128250 A1 | 5/2021 | Chav et al. | |
| 2021/0156676 A1 | 5/2021 | Messerly et al. | |
| 2021/0298680 A1 | 9/2021 | Sowards et al. | |
| 2021/0378759 A1 | 12/2021 | Komp et al. | |
| 2021/0402144 A1 | 12/2021 | Messerly et al. | |
| 2022/0071589 A1 | 3/2022 | Sowards et al. | |
| 2023/0036150 A1 | 2/2023 | Wiles et al. | |
| 2024/0060770 A1 | 2/2024 | Ha et al. | |
| 2024/0148466 A1 | 5/2024 | Schneider | |
| 2024/0335237 A1* | 10/2024 | Sowards | ............... G16H 40/63 |

OTHER PUBLICATIONS

Xu et al., "Shape Sensing with Rayleigh Backscattering Fibre Optic Sensor," Sensors, Jul. 21, 2020, 20(14):1-19.

Abiodun et al., "State-of-the-art in artificial neural network applications: A survey," Heliyon, Nov. 13, 2018, 4(11):1-41.

Amirsolaimani et al. "High sensitivity magnetometer using nanocomposite polymers with large magneto-optic response," Optics Letters, Oct. 2018, 43(19):4615-4618.

Arm.com [online], "Arm AI: Bringing AI Technologies to Life," 2023, retrieved on Feb. 8, 2023, retrieved from URL<https://www.arm.com/products/silicon-ip-cpu/ai-platform>,12 pages.

Boccaccio et al., "Calibration of a Fiber Bragg Grating as Ultra-Sensitive Strain Gauge," LNL Annual Report, Appl., Gen. and Interdisc. Phys. Instrumentation, 2010, 191-192.

Bock et al., "Automatic calibration of a fiber-optic strain sensor using a self-learning system," IEEE Transactions on Instrumentation and Measurement, Apr. 1994, 43(2):341-346.

Broomhead et al., "Multivariable Functional Interpolation and Adaptive Networks," Complex Systems, 1988, 2:321-355.

Cheng et al., "Calibrating static measurement data from distributed fiber optics by the integration of limited FBG sensors based on the extended kernel regression method," Measurement Science and Technology, Sep. 17, 2019, 30(12):125102 (abstract only).

Coral.ai [online], "Products: Helping you bring local AI to applications from prototype to production," 2020, retrieved on Feb. 8, 2020, retrieved from URL<https://coral.ai/products/>, 19 pages.

Ding et al., "Distributed Optical Fiber Sensors Based on Optical Frequency Domain Reflectometry: A review," Sensors, Apr. 3, 2018, 31 pages.

Duncan et al., "High-accuracy fiber-optic shape sensing," Proc. SPIE 6530, Sensor Systems and Networks: Phenomena, Technology, and Applications for NDE and Health Monitoring, Apr. 10, 2007, 65301S, 11 pages (abstract only).

Fbgs.com [online], "FBG Principle," available on or before Jun. 14, 2021, retrieved on Jan. 10, 2023, retrieved from URL<https://fbgs.com/technology/fbg-principle/>, 8 pages.

Floris et al., "Fiber Optic Shape Sensors: A comprehensive review," Optics and Lasers in Engineering, Apr. 2021, 32 pages.

Galloway et al., "Fiber Optic Shape Sensing for Soft Robotics," Soft Robotics, Oct. 2019, 6(5):671-684.

Hornik, "Multilayer Feedforward Networks are Universal Approximators," Neural Networks, 1989, 2(5):359-366.

IBM.com [online], "What is a neural network?," Dec. 16, 2021, retrieved on Feb. 8, 2023, retrieved from URL<https://www.ibm.com/topics/neural-networks>, 11 pages.

(56)                    References Cited

OTHER PUBLICATIONS

IBM.com [online], "What is machine learning?," Oct. 12, 2020, retrieved on Feb. 8, 2020, retrieved from URL<https://www.IBM.com/topics/machine-learning>, 13 pages.

Inaccel.com [online], "CPU, GPU, FPGA or TPU: Which one to choose for my Machine Learning training?," Dec. 17, 2018, retrieved on Feb. 8, 2023, retrieved from URL<https://inaccel.com/cpu-gpu-fpga-or-tpu-which-one-to-choose-for-my-machine-learning-training/>, 9 pages.

Intel.com [online], "FPGA vs. GPU for Deep Learning," 2020, retrieved on Feb. 8, 2023, retrieved from URL<https://www.intel.com/content/www/us/en/artificial-intelligence/programmable/fpga-gpu.html>, 6 pages.

Issatayeva et al., "Design and analysis of a fiber-optic sensing system for shape reconstruction of a minimally invasive surgical needle." Sci Rep., Apr. 2021, 11(1):8609, 12 pages.

Jäckle et al., "3D Catheter Guidance including Shape Sensing for Endovascular Navigation," Proceedings vol. 11315, Medical Imaging 2020: Image-Guided Procedures, Robotic Interventions, and Modeling, Mar. 16, 2020, 9 pages.

Jäckle et al., "Three-dimensional guidance including shape sensing of a stentgraft system for endovascular aneurysm repair," International Journal of Computer Assisted Radiology and Surgery, May 7, 2020, 15:1033-1042 (abstract only).

Kautzman et al., "Calibration and Testing of Distributed Fiber Optic Sensors for Detection of High Energy Radiation," Journal of Directed Energy, Oct. 2018, 15 pages.

Khan et al., "Multi-core Optical Fibers with Bragg Gratings as Shape Sensor for Flexible Medical Instruments," IEEE Sensors Journal, Jul. 15, 2019, 19(14):5878-5884.

Klug et al., "Test and calibration of 20 FBG based strain transducers," Materials Science, Jul. 1, 2015, 11 pages.

Lally et al., "Fiber optic shape sensing for monitoring of flexible structures," Proc. SPIE 8345, Sensors and Smart Structures Technologies for Civil, Mechanical, and Aerospace Systems 2012, Apr. 6, 2012, 83452Y, 9 pages (abstract only).

Lazarev et al., "Fiber Bragg gratings strain measuring system and a sensor calibration setup based on mechanical nanomotion transducer," Proc. of SPIE vol. 10329, Jun. 26, 2017, 103292F-1, 7 pages.

Liang et al., "A Comprehensive Study of Optical Frequency Domain Reflectometry," IEEE Access, vol. 9, Jan. 2021, 22 pages.

Miller et al., "Shape sensing using distributed fiber optic strain measurements," Proc. SPIE 5502, Second European Workshop on Optical Fibre Sensors, Jun. 9, 2004, 4 pages (abstract only).

Monet et al., "High-Resolution Optical Fiber Shape Sensing of Continuum Robots: A Comparative Study," 2020 IEEE International Conference on Robotics and Automation (ICRA), May 31-Aug. 31, 2020, 8877-8883 (abstract only).

Moore et al., "Shape sensing using multi-core fiber optic cable and parametric curve solutions," Opt. Express, Jan. 30, 2012, 20(3):2967-2973.

Pan et al., "A Survey on Transfer Learning," IEEE Transactions on Knowledge and Data Engineering, Oct. 2010, 22(10):1345-1359.

Park et al., "Universal Approximation Using Radial-Basis-Function Networks," Neural Computation, Jun. 1991, 3(2):246-257.

Primo.ai [online], "Processing Units—CPU, GPU, APU, TPU, VPU, FPGA, QPU," Nov. 16, 2022, retrieved on Feb. 8, 2023, retrieved from URL<http://primo.ai/index.php?title=Processing_Units—_Cpu, GPU, APU, TPU, VPU, FPGA, QPU>, 20 pages.

Principles of Neurodynamics, Perceptrons and the Theory of Brain Mechanisms, Cornell Aeronautical Laboratory, Inc F., Rosenblatt, Mar. 15, 1961, 626 pages.

Roths et al., "Strain calibration of optical FBG-based strain sensors," Proc. SPIE 7653, Fourth European Workshop on Optical Fibre Sensors, Sep. 8, 2010, 4 pages (abstract only).

Rumelhart et al., "Learning representations by back-propagating errors," Nature, Oct. 1, 1986, 4 pages.

Schmidhuber, "Deep learning in neural networks: An overview," CoRR, Submitted on Apr. 30, 2014, arXiv:1404.7828, 88 pages.

Tan et al., "A Survey on Deep Transfer Learning," CoRR, submitted on Aug. 6, 2018, arXiv:1808.01974, 10 pages.

Tan et al., "High-precision calibration method for fiber Bragg grating strain sensing based on an optical lever," Optical Fiber Technology, Jan. 2021, 61:2021 (abstract only).

Towardsdatascience.com [online], "Machine Learning and Signal Processing," Aug. 9, 2020, retrieved on Feb. 8, 2023, retrieved from URL<https://towardsdatascience.com/machine-learning-and-signal-processing-103281d27c4b>, 27 pages.

Weiss et al., "A survey of transfer learning," J Big Data, May 28, 2016, 3(9):1-40.

Wikipedia.org [online], "Dielectric," available on or before May 23, 2022, via Internet Archive: Wayback Machine URL<https://web.archive.org/web/20220523185612/https://en.wikipedia.org/wiki/Dielectric>, retrieved on May 14, 2024, URL<https://en.wikipedia.org/wiki/Dielectric>, 13 pages.

Wikipedia.org [online], "Group method of data handling," Nov. 25, 2022, retrieved on Feb. 8, 2023, retrieved from URL<https://en.wikipedia.org/wiki/Group_method_of_data_handling>, 6 pages.

Wikipedia.org [online], "Gyroelectromagnetism," available on or before Jun. 16, 2020, via Internet Archive: Wayback Machine URL<https://web.archive.org/web/20200616174223/https://en.wikipedia.org/wiki/Gyroelectromagnetism>, retrieved on May 14, 2024, URL<https://en.wikipedia.org/wiki/Gyroelectromagnetism>, 1 page.

Wikipedia.org [online], "Light" available on or before May 24, 2022, via Internet Archive: Wayback Machine URL<https://web.archive.org/web/20220324071627/https://en.wikipedia.org/wiki/Light>, retrieved on May 14, 2024, URL<https://en.wikipedia.org/wiki/Light>, 13 pages.

Wikipedia.org [online], "Magnetic field," available on or before May 24, 2022, via Internet Archive: Wayback Machine URL<https://web.archive.org/web/20220324083432/https://en.wikipedia.org/wiki/Magnetic_field>, retrieved on May 14, 2024, URL<https://en.wikipedia.org/wiki/Magnetic field>, 30 pages.

Wikipedia.org [online], "Magneto-optic effect," available on or before May 12, 2022, via Internet Archive: Wayback Machine URL<https://web.archive.org/web/20220512061613/https://en.wikipedia.org/wiki/Magneto-optic_effect>, retrieved on May 14, 2024, URL<https://en.wikipedia.org/wiki/Magneto-optic_effect>, 4 pages.

Wikipedia.org [online], "Permittivity," available on or before May 12, 2022, via Internet Archive: Wayback Machine URL<https://web.archive.org/web/20220512101334/https://en.wikipedia.org/wiki/Permittivity>, retrieved on May 14, 2024, URL<https://en.wikipedia.org/wiki/Permittivity>, 13 pages.

Wikipedia.org [online], "Physics," available on or before May 24, 2022, via Internet Archive: Wayback Machine URL<https://web.archive.org/web/20220324083216/https://en.wikipedia.org/wiki/Physics>, retrieved on May 14, 2024, URL<https://en.wikipedia.org/wiki/Physics>, 27 pages.

Wikipedia.org [online], "Polarization," available on or before May 24, 2022, via Internet Archive: Wayback Machine URL<https://web.archive.org/web/20220324042832/https://en.wikipedia.org/wiki/Polarization_(waves)>, retrieved on May 14, 2024, URL<https://en.wikipedia.org/wiki/Polarization_(waves)>, 25 pages.

Wikipedia.org [online], "Tensor," available on or before May 20, 2022, via Internet Archive: Wayback Machine URL<https://web.archive.org/web/20220520184616/https://en.wikipedia.org/wiki/Tensor>, retrieved on May 14, 2024, URL<https://en.wikipedia.org/wiki/Tensor>, 21 pages.

Wikipedia.org [online], "Transparency and translucency," available on or before May 25, 2022, via Internet Archive: Wayback Machine URL<https://web.archive.org/web/20220525102539/https://en.wikipedia.org/wiki/Transparency_and_translucency>, retrieved on May 14, 2024, URL<https://en.wikipedia.org/wiki/Transparency_and_translucency>, 11 pages.

Wikipedia.org [online], "Universal approximation theorem," Feb. 5, 2023, retrieved on Feb. 8, 2023, retrieved from URL<https://en.wikipedia.org/wiki/Universal_approximation_theorem>, 9 pages.

Xu et al., "Curvature, Torsion, and Force Sensing in Continuum Robots Using Helically Wrapped FBG Sensors," IEEE robotics & automation letters, Feb. 17, 2016, 1(2):1052-1059.

(56)          References Cited

OTHER PUBLICATIONS

Yuksel et al., "Optical Frequency Domain Reflectometry: A Review,"
11th International Conference on Transparent Optical Networks,
Jun. 2009, 5 pages.

* cited by examiner

<u>700</u>

Generate random shape

<u>702</u>

Set initial conditions

<u>704</u>

Calculate T(s), N(s), and B(s) along shape

<u>706</u>

Generate additional fiber cores

<u>708</u>

Determine distances and angles of cores around center of MFOS

<u>710</u>

Determine curvature of each core

<u>712</u>

Determine strain on each core

<u>714</u>

Pair strain data with shape data to form training data

<u>716</u>

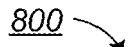
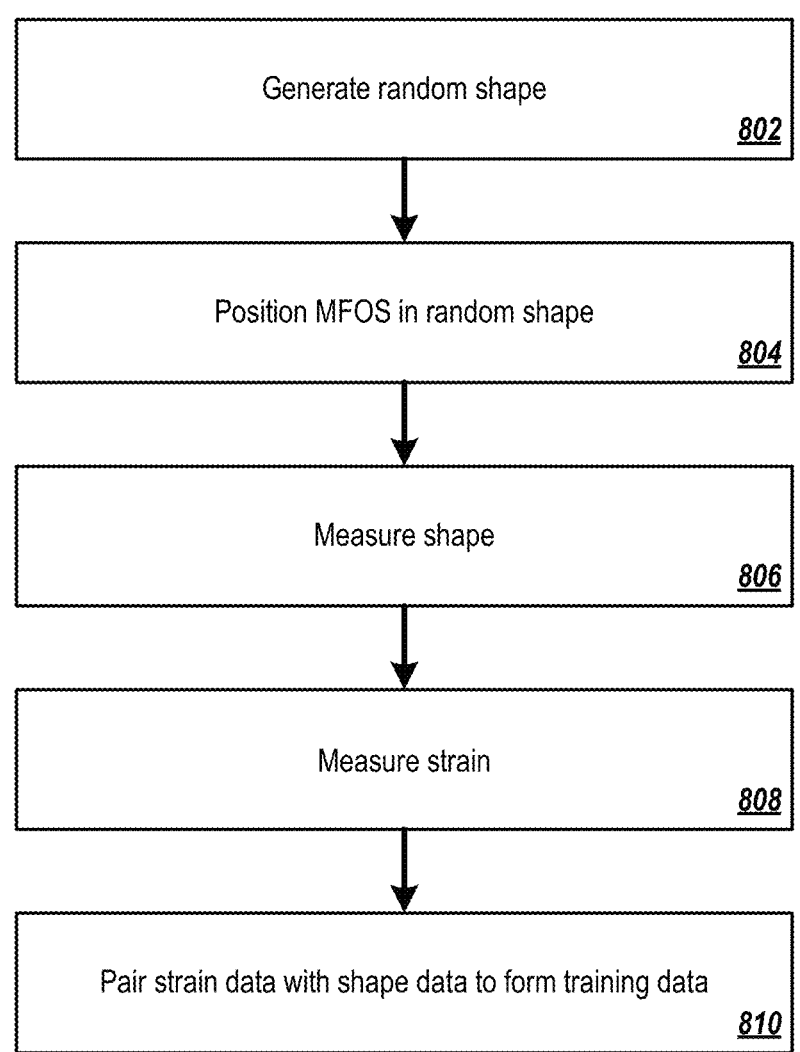
_800_
| |
|---|
| Generate random shape _802_ |
| |
|---|
| Position MFOS in random shape _804_ |
| |
|---|
| Measure shape _806_ |
| |
|---|
| Measure strain _808_ |
| |
|---|
| Pair strain data with shape data to form training data _810_ |
FIG. 8

Strain data 1002

Shape Learning Machine 1004

MFOS shape 1006

1008

1000

_1100_

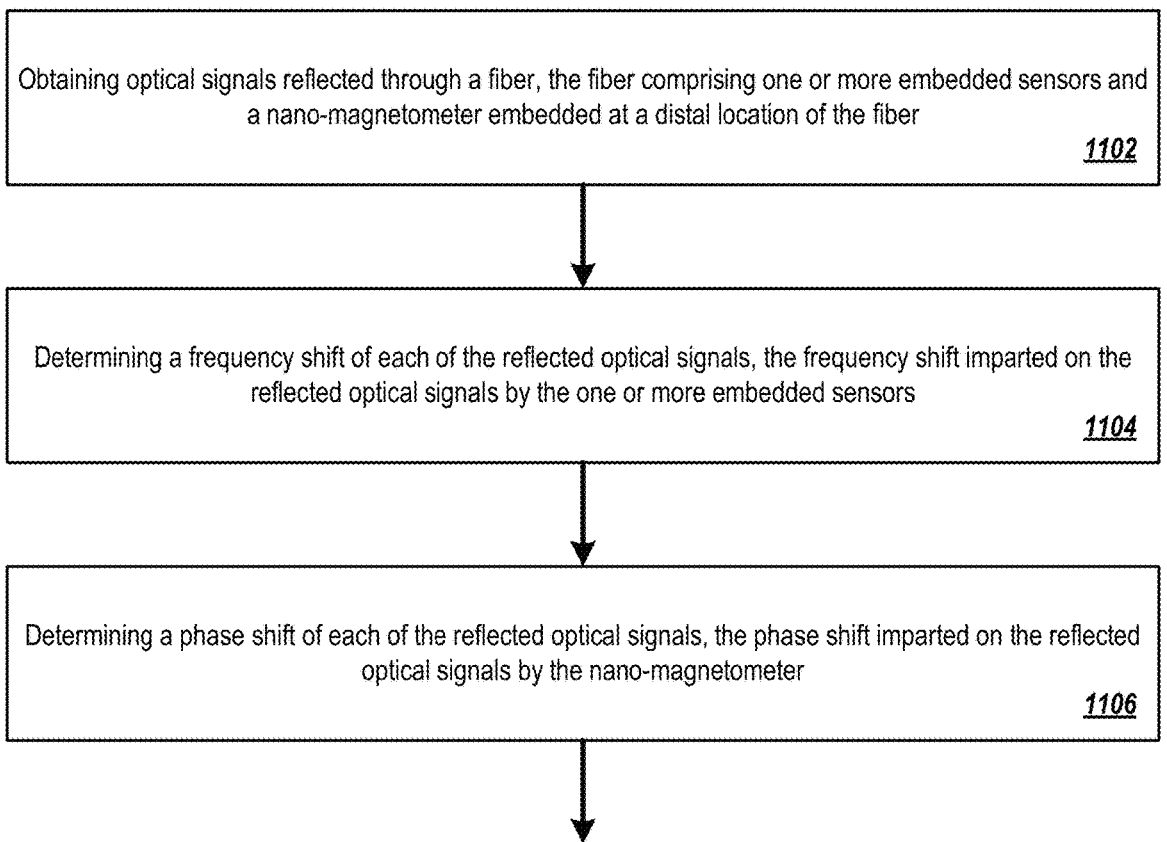

Obtaining optical signals reflected through a fiber, the fiber comprising one or more embedded sensors and a nano-magnetometer embedded at a distal location of the fiber

_1102_

Determining a frequency shift of each of the reflected optical signals, the frequency shift imparted on the reflected optical signals by the one or more embedded sensors

_1104_

Determining a phase shift of each of the reflected optical signals, the phase shift imparted on the reflected optical signals by the nano-magnetometer

_1106_

Determining one or more characteristics of the fiber using the determined frequency shift and the phase shift of each of the reflected optical signals, wherein the one or more characteristics of the fiber comprises a shape of the fiber and a location of the fiber in relation to an external reference    _1108_

FIBER OPTIC SHAPE SENSING MANAGEMENT

CROSS-REFERENCE TO RELATED APPLICATIONS

This application claims the benefit of U.S. Provisional Application No. 63/502,240 filed on May 15, 2023, which is incorporated herein by reference.

TECHNICAL FIELD

This specification relates to tracking an optical fiber in an electromagnetic field.

BACKGROUND

Electromagnetic Tracking (EMT) systems are used to aid in locating instruments and patient anatomy in medical procedures. These systems utilize a magnetic transmitter in proximity to one or more magnetic sensors. The one or more sensors can be spatially located relative to the transmitter and sense magnetic fields produced by the transmitter.

SUMMARY

Some tracking systems can provide characteristics of an optical fiber used in medical procedures. The characteristics can include, for example, pose, shape, and position of the optical fiber, to name some examples. In further detail, the tracking systems can locate instruments and make measurements with respect to a patient anatomy using the provided characteristics of the optical fiber. These medical procedures can span many domains and can include, for example, surgical interventions, diagnostic procedures, imaging procedures, radiation treatment, etc., to name a few examples. In some cases, the optical fiber can be attached to an instrument in a medical procedure to provide characteristics of the instrument, e.g., position, orientation, and shape, to name a few. In some examples, the characteristics of the instrument can include one or more of the aforementioned characteristics. While many methodologies may be employed to provide characteristics of the optical fiber, artificial intelligence techniques, such as machine-learning, can exploit the characteristics of the optical fiber for training and evaluation. By developing such techniques to determine various characteristics of the optical fiber, applications and computations for tracking an instrument in a medical procedure can be improved.

In some implementations, the tracking system can utilize electromagnetic tracking technology for determining characteristic information of the fiber, such as pose information. Specifically, electromagnetic tracking technology can utilize sensors that are small enough to approach the diameters of optical fibers for measuring pose, while maintaining the levels of sensitivity to electromagnetic fields that are required for tracking. Furthermore, by utilizing electromagnetic tracking technology, the tracking systems can interpret sensed magnetic signals using light in an optical fiber to obtain or measure pose.

In some implementations, the tracking system can utilize various components of the electromagnetic tracking technology for shape sensing. In some examples, the tracking system can include a nano-magnetometer, an electromagnetic tracking system, and a fiber optic shape sensing system. In further detail, the nano-magnetometer can be embedded at a distal end of the optical fiber. In some examples, the optical fiber can be equipped with one or more Bragg gratings. The tracking system can utilize a tunable laser, covering a range of wavelengths, which transmits light down the optical fiber. The tracking system can utilize a spectrometer and a computer system to interpret the reflected light.

The reflected light can carry information about the magnetic fields sensed by the nano-magnetometer. Specifically, the nano-magnetometer can sense the magnetic fields and apply the sensed magnetic fields to the transmitted light through a physical process that shifts the phase of the light after it reflects from the sensors. Additionally, the electromagnetic tracking system can observe wavelength shifts in the reflected light, which can be caused by the bending and twisting of the fiber, which can indicate a measure of strain introduced in the optical fiber. The electromagnetic tracking system can analyze the phase shifts imparted by the nano-magnetometer and the wavelength shifts imparted by the fiber to estimate the characteristics of the optical fiber, e.g., such as the strain of the fiber. In response, the tracking system can estimate the curvature, angle of curvature, and by extension, the shape of the fiber. In some examples, one of the wavelengths emitted from the laser is used in conjunction with the nano-magnetometer to sense magnetic fields and track the location of the sensor. In some examples, the tracking system can use other wavelengths emitted from laser for shape estimation. This process will be further described below.

In one general aspect, a method performed by one or more computing devices includes: obtaining optical signals reflected through a fiber, the fiber comprising one or more embedded sensors and a nano-magnetometer embedded at a distal location of the fiber; determining a frequency shift of each of the reflected optical signals, the frequency shift imparted on the reflected optical signals by the one or more embedded sensors; determining a phase shift of each of the reflected optical signals, the phase shift imparted on the reflected optical signals by the nano-magnetometer; and determining one or more characteristics of the fiber using the determined frequency shift and the phase shift of each of the reflected optical signals, wherein the one or more characteristics of the fiber comprises a shape of the fiber and a location of the fiber in relation to an external reference.

Other embodiments of this and other aspects of the disclosure include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The foregoing and other embodiments can each optionally include one or more of the following features, alone or in combination. For example, one embodiment includes all the following features in combination.

In some implementations, determining the one or more characteristics of the fiber includes determining the location of the fiber using at least the determined phase shift of each of the reflected optical signals.

In some implementations, determining the one or more characteristics of the fiber includes determining the shape of the fiber using at least the determined frequency shift of each of the reflected optical signals.

In some implementations, the method includes instructing a tunable laser to transmit the optical signals through the fiber.

In some implementations, the optical signals include light having a range of wavelengths.

In some implementations, determining the phase shift of each of the reflected optical signals further includes: determining one or more magnetic fields sensed by the nano-magnetometer from the determined phase shift of each of the reflected optical signals; and identifying a location of the nano-magnetometer at the distal location of the fiber using the one or more determined magnetic fields.

In some implementations, determining the frequency shift of each of the reflected optical signals further includes determining a measure of bend at various locations along the fiber using the determined frequency shift of each of the reflected optical signals.

In some implementations, determining the one or more characteristics of the fiber using the determined frequency shift and the determined phase shift of each of the reflected optical signals further includes: determining a strain of the fiber using the determined measure of bend at the various locations along the fiber using the determined frequency shift, wherein the determined frequency shift of each of the reflected optical signals represents: (i) a location of the strain of the fiber and (ii) a location of each of the one or more embedded sensors in the fiber; wherein the one or more characteristics of the fiber comprises (i) a curvature of the fiber at the location of the strain (ii) an angle of the curvature at the location of the strain, (iii) the shape of the fiber, and (iv) the location of the fiber.

In some implementations, the method includes: estimating the shape of the fiber by combining, at each location of the strain, the curvature of the fiber and the angle of the curvature; and determining the location of the fiber using (i) the estimated shape of the fiber and (ii) the identified location of the nano-magnetometer, wherein the external reference represents the identified location of the nano-magnetometer.

In some implementations, the estimated shape of the fiber indicates a shape of the fiber in three-dimensional spatial coordinates, and wherein the estimated shape of the fiber comprises one or more of an orientation of a center of the fiber, a first radial axis of the fiber, and a second radial axis of the fiber.

In some implementations, the one or more embedded sensors comprise one or more Fiber Bragg Gratings (FBG) embedded at various locations along the fiber.

In some implementations, the fiber comprises a plurality of cores, wherein the nano-magnetometer reflects a portion of the optical signals through a first subset of the cores of the plurality of the cores and the one or more embedded sensors reflects a portion of the optical signals through a second subset of the cores, wherein the first subset of the cores are different from the second subset of the cores.

In some implementations, the method includes: training a machine-learning model to predict the one or more characteristics of the fiber using the determined frequency and the phase shift of each of the reflected optical signals; and applying the trained machine-learning model.

In some implementations, the method includes shifting a wavelength of the nano-magnetometer within an operating range of an interrogator.

In some implementations, the fiber is positioned in a surgical environment.

In one general aspect, a system includes: a fiber; one or more sensors and a nano-magnetometer embedded in the fiber; and an interrogator device configured to: transmit optical signals through the fiber; receive reflected optical signals from the fiber; determine a frequency shift of each of the reflected optical signals, the frequency shift imparted on the reflected optical signals by the one or more embedded sensors; determine a phase shift of each of the reflected optical signals, the phase shift imparted on the reflected optical signals by the nano-magnetometer; and determine one or more characteristics of the fiber using the determined frequency shift and the phase shift of each of the reflected optical signals, wherein the one or more characteristics of the fiber comprises a shape of the fiber and a location of the fiber in relation to an external reference.

The subject matter described in this specification can be implemented in various embodiments and may result in one or more of the following advantages. By embedding a nano-magnetometer into a distal end of the optical fiber, a minimum number of components can be utilized to identify a location of the optical fiber, such as within a surgical theater. Typically, one or more sensors can be embedded in the patient for tracking the location of the optical fiber. However, these sensors can be eliminated from the system and a nano-magnetometer can provide enhanced functionality in its place while reducing the overall footprint of components within a patient. The incorporation of one or more sensors embedded in the patient creates an increase in the number of wires embedded in the patient. However, by embedding a nano-magnetometer into the optical fiber, the number of wires can be reduced due to the removal of the sensors, which reduces the amount of hardware required to monitor and track the location of the optical fiber within the patient.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 8 is another flowchart of operations of a training data generator to physically generate training data to train an optical fiber characteristic sensing machine-learning system.

FIG. 11 is a flowchart of determining characteristics of an optical fiber.

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

Figure 1:
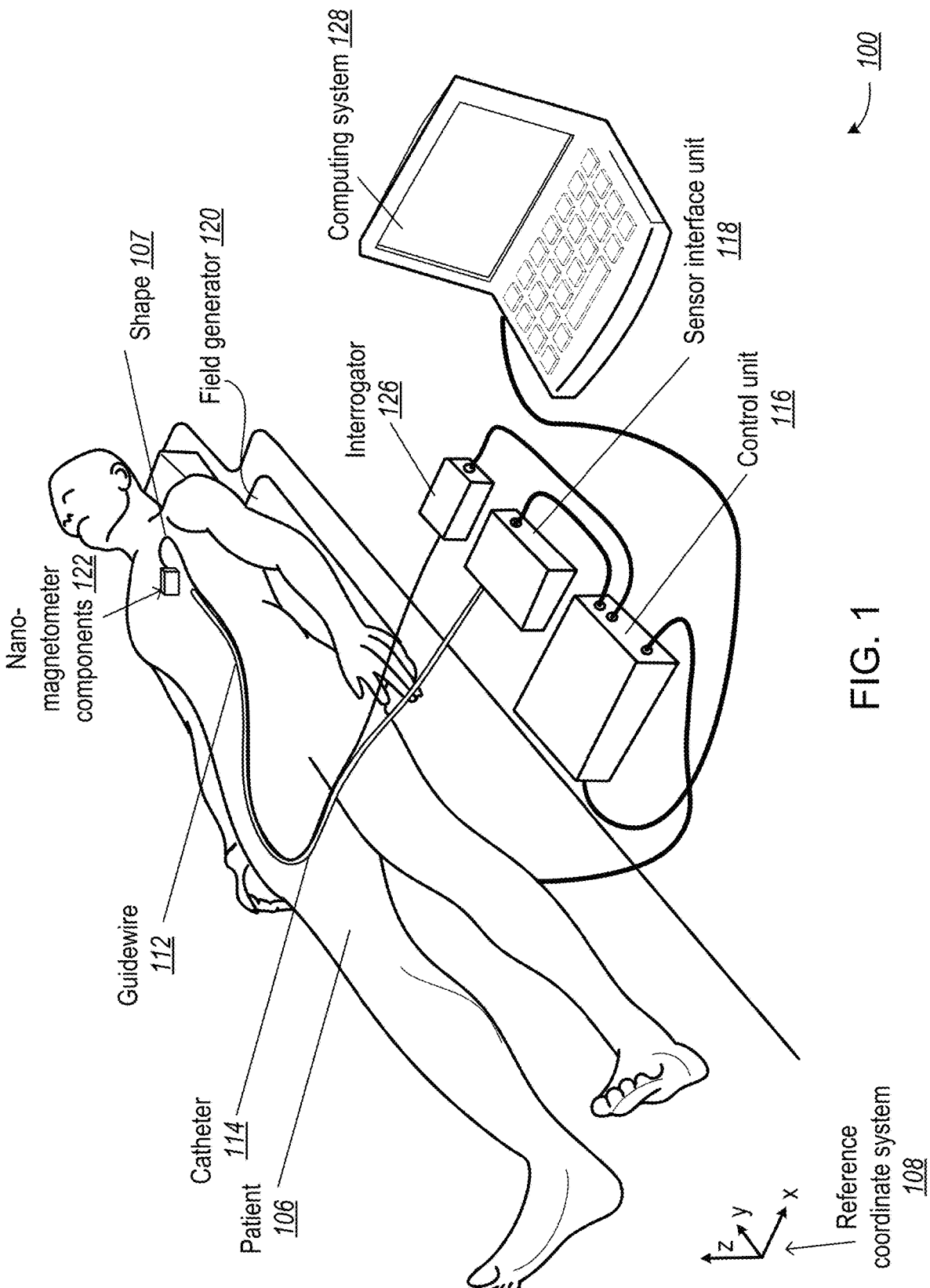
FIG. 1 is a schematic diagram of an example system for providing characteristics of a tracked optical fiber.

Fiber optic shape sensing (FOSS) can include applications in spatial navigation for medical procedures and other applications. FOSS can be implemented by utilizing a tracking system that determines characteristics of an optical fiber. Specifically, the tracking system can transmit a light beam through the optical fiber and measure the reflected light to analyze the characteristics of the optical fiber. In further detail, the tracking system can identify the characteristics of the optical fiber because the reflected light can carry useful information encoded in wavelengths shifts—caused by the bending and twisting of the optical fiber. In some cases, the wavelength shifts can be analyzed by a spectrometer and a computer system to infer a measure of strain in the optical fiber. The strain measurements can be analyzed to estimate curvature and angle of curvature of the optical fiber. The estimated curvature, angle of curvature, and other characteristics can be used to estimate the shape of the optical fiber.

In some implementations, the tracking system can utilize multiple methods to relate strain to wavelength shifts in the field of FOSS. In some examples, an implementer of a system that includes the optical fiber can inscribe the optical fiber with Bragg gratings. Bragg gratings can be designed and/or configured to reflect a specific wavelength, known as a Bragg wavelength. The Bragg wavelength can be a function of the strain of the optical fiber. In some examples, an implementer of the system can incorporate microscopic imperfections on the fiber and can exploit a natural process known as Rayleigh backscattering. As a result, the wavelength of the backscattered light, e.g., the transmitted light reflected off the microscopic imperfections on the fiber, also shifts as a function of strain.

In some implementations, the tracking system can generate a shape estimate of the optical fiber. The shape estimate can be a collection of point coordinates in three dimensions, which can be expressed with respect to a common origin. The shape origin can be chosen, arbitrarily, to be any point along the measurable segment of the fiber. In some implementations, the shape of the optical fiber can exist in its own frame of reference. This frame of reference can be unrelated to other components and therefore not localized in the larger context of a surgical environment. As such, it is beneficial to locate the position of the fiber shape's origin in relation to an external reference.

In some implementations, a system can utilize an electromagnetic tracking system and a fiber optic shape sensing system. The electromagnetic tracking system can include a nano-magnetometer that is embedded to a distal end of an optical fiber. The nano-magnetometer can sense magnetic fields radiated within the system and can apply a phase shift to the transmitted light, an amount of the phase shift being directly proportional to an amount of the sensed magnetic fields. The nano-magnetometer can transmit the reflected phase-shifted light down the optical fiber.

In some examples, the optical fiber can be equipped with one or more Bragg gratings. In some examples, the optical fiber can incorporate microscopic imperfections and exploit the backscattered light off the imperfections using the Rayleigh method.

In some implementations, the system can utilize a tunable laser for transmitting light through the optical fiber. The light can cover a range of wavelengths, for example. The system can utilize a spectrometer and a computer system that can interpret the light reflected from the optical fiber. The reflected light can carry information about the magnetic fields sensed by the nano-magnetometer through a physical process that shifts the phase of the light after it reflects from the sensor. Additionally, the system can observe wavelength shifts or frequency shifts in the reflected light caused by the bending and twisting of the optical fiber. The bending and twisting of the optical fiber can offer a measure of strain in the optical fiber. The strain in the optical fiber can be used to estimate the curvature, angle of curvature, and other characteristics of the optical fiber. The system can then determine the shape of the fiber utilizing the estimated curvature, angle curvature, and the other characteristics of the optical fiber. In some examples, one of the transmitted wavelengths emitted from the tunable laser is used in conjunction with the nano-magnetometer to sense magnetic fields and track the location of the sensor, e.g., position of nano-magnetometer. The shape of the fiber and the position of the nano-magnetometer can be utilized to provide characteristics indicative of the optical fiber. Other wavelengths emitted from the transmitted laser can be used for shape estimation of the optical fiber.

FIG. 1 is a schematic diagram of an example electromagnetic tracking system 100 that is implemented in the surgical environment (e.g., a surgical theater). The tracking system 100 can collect information from various components to determine the location of one or more medical devices, e.g., scalpels, probes, guidewires, etc., and equipment, etc. The tracking system 100 can attach to or embed a nano-magnetometer 122 in a guidewire 112 for tracking the guidewire 112 in various medical procedures involving a patient. The guidewire 112 can include an optical fiber. Tracking the guidewire 112 can be useful to determine the position of the guidewire 112 within the patient, e.g., the patient's vasculature. Once the shape, position, and other characteristics of the guidewire 112 are determined, the guidewire 112 can be used to guide other medical instruments, e.g., catheter, through the patient, e.g., the patient's vasculature.

In some implementations, the tracking system 100 can employ tracking techniques that provide Six Degrees of Freedom (6DOF). 6DOF tracking can be used in medical applications, e.g., tracking medical equipment in surgical theaters, to track one or more objects, e.g., a medical device such as a scalpel, one or more robotic arms, etc., thereby determining and identifying the respective three-dimensional location, orientation, etc. of the object or objects for medical professionals, e.g., a surgeon. Such tracking can be employed for various applications such as providing guidance to professionals, and in some cases may reduce reliance on other imaging modalities, such as fluoroscopy, which can expose patients, health care providers, and others to ionizing radiation that can potentially create health risks.

In some implementations, a nano-magnetometer can be a device that measures a magnetic field or magnetic fields. The nano-magnetometer can be configured to measure direction, strength, or relative change of a magnetic field at a particular location, e.g., a distal end of the optical fiber. For example, a nano-magnetometer can be constructed small enough to approach a diameter of the optical fiber used for shape-sensing. Despite the small size of the nano-magnetometer, the functionality of the nano-magnetometer remains and can detect various levels of sensitivity in electromagnetic (EM) fields that are required for tracking of the optical fiber. In response to measuring various levels of sensitivity in electromagnetic fields, the nano-magnetometer can produce signals that reflect the measured characteristics. The measured characteristics of the EM field depend on the position and orientation of the nano-magnetometer relative to the guidewire 112. The nano-magnetometer can measure the characteristics of the EM field and provide measurement information to a computing device such as a computer system, e.g., data representing EM measurement information is imparted on reflected light transmitted by the interrogator 126. From the provided measurement information, the computing device can determine the position, shape, orientation, and other characteristics etc. of the optical fiber. In some examples, a single nano-magnetometer can provide position and orientation in 5DOF. In some examples, multiple nano-magnetometers can provide position and orientation in 6DOF. Using this technique, the position, orientation, shape, etc., of a medical device can be determined and processed by the computing device, e.g., the computing device identifies the position, location, and shape of a medical device and can graphically represent the medical device, e.g., the optical fiber, etc., in images such as registered medical images, etc.

To produce understandable tracking data, a reference coordinate system is established by the tracking system 100. The relative pose, e.g., location, position, of the nano-magnetometer 122 located at the distal end of the optical fiber can be determined relative to a reference coordinate system 108, tied to the field generator 120. Specifically, the nano-magnetometer 122 can define the reference coordinate system 108 relative to the patient 106 because the nano-magnetometer 122 is attached to the patient 106. In some implementations, the tracking system 100 can utilize various electromagnetic sensors in conjunction with the nano-magnetometer 122 to enhance the detection of the coordinate system 108. In some implementations, by establishing the reference coordinate system 108 using the nano-magnetometer 122, a location and orientation of other electromagnetic sensors or a location and orientation of a guidewire 112 can be determined relative to the reference coordinate system 108. Defining one reference coordinate system allows data to be viewed from one frame of reference, for example, location data associated with the nano-magnetometer, location data associated with the patient, etc., are each placed on the same frame of reference so the data is more easily understandable. In some implementations, a catheter 114 is inserted over the guidewire 112 after the guidewire 112 is inserted into the patient.

In this particular implementation, a control unit 116 and a sensor interface unit 118 are configured to resolve signals produced by the reflected light transmitted by the interrogator 126. For example, the control unit 116 and the sensor interface unit 118 can receive the signals produced by the reflected light, e.g., through a wired or wireless connection. The control unit 116 and the sensor interface unit 118 can determine the pose, location, and other characteristics of the nano-magnetometer 122 using electromagnetic tracking methodologies. The pose of the nano-magnetometer 122 can define the reference coordinate system 108, as discussed above. The pose of the nano-magnetometer 122 can provide information about the leading segment of the guidewire 112. The optical based tracking system 100 may employ techniques for tracking and identifying the respective three-dimensional location, orientation, shape, etc. of objects for medical professionals, such as using optical tracking methodologies.

In some implementations, the geometry and dimensions of the guidewire 112 can vary. In some examples, the guidewire 112 may have a maximum diameter of approximately 0.8 millimeters (mm). In some examples, the guidewire 112 may have a diameter larger or smaller than approximately 0.8 mm. The guidewire 112 can be used to guide medical equipment or measurement equipment through the patient (e.g., through the patient's vasculature). In some examples, the guidewire 112 may guide optical fibers through the patient. In some examples, the optical fiber may guide the guidewire 112 through the patient according to a navigational context. While the guidewire 112 may have a cylindrical geometry, one or more other types of geometries may be employed (e.g., geometries with rectangular cross sections). In some implementations, a guidewire 112 may include a bundle of wires.

In some implementations, a field generator 120 can reside beneath the patient 106, e.g., located under a surface that the patient is positioned on, embedded in a surface that the patient lays upon—such as a tabletop, etc. to emit electromagnetic fields that are sensed by the nano-magnetometer 122. In some examples, the field generator 120 is an Aurora Tabletop Field Generator (TTFG), although other field generator techniques and/or designs can be employed.

In some implementations, the nano-magnetometer 122 can use the one or more electromagnetic fields emitted by the field generator 120 to produce location information of the nano-magnetometer 122. Specifically, the nano-magnetometer 122 can sense the electromagnetic fields emitted by the field generator 120 and obtain the sensed electromagnetic fields. Based on the obtained electromagnetic fields, the nano-magnetometer 122 can impart the sensed electromagnetic field on a reflected transmitted light, for example, and the interrogator 126 and the computing system 128 can determine location information of the nano-magnetometer 122 using the information imparted on the reflected transmitted light. The location information can be, for example, three-dimensional coordinates, spatial coordinates, geographical coordinates, or other types of coordinates. As will be further described below, the nano-magnetometer 122 can impart the generated sensed electromagnetic field on the reflected light by affecting the reflected light's phase.

The location information, e.g., the position, orientation, and other information, of a tracked nano-magnetometer 122 can refer to a direction the tracked sensor is facing with respect to a global reference point, e.g., the reference coordinate system 108, and can be expressed similarly by using a coordinate system and represented, for example, as a vector of orientation coordinates, e.g., azimuth ($\psi$) and altitude ($\theta$)) or Cartesian coordinates, e.g., x, y, and z. In some examples, the tracked nano-magnetometer 122 can provide location information in 5DOF. The tracking system 100 can operate to determine characteristics of an optical fiber, as discussed below. In some examples, the tracking system 100 can utilize the information provided by the nano-magnetometer 122 and information provided by the other examples within the optical fiber to characterize the optical fiber in terms of 6DOF characteristics. The 6DOF characteristics can allow for measurement of position and orientation information of a tracked nano-magnetometer 122 related to a forward/back position, up/down position, left/right position, azimuth, altitude, and roll, and other characteristics.

In some implementations, the optical fiber can form one or multiple shapes as it extends into and through the body of the patient 106. The interrogator 126 can transmit light down the optical fiber and the reflected light can be used to track, for example, the location, orientation, shape, and other characteristics of measured segments of the optical fiber. In response, the tracking system 100, e.g., the computing system 128, can determine information indicative of the optical fiber's characteristics.

In the example shown in FIG. 1, a hook shape 107 is produced by the guidewire 112, which can be resolved by the system 100. For example, an interrogator 126 can transmit fiber optic signals, such as light, down the optical fiber. In response, the interrogator 126 can receive the reflected fiber optic signals, e.g., one or more waveforms that are reflected back, through the optical fiber. The received fiber optic signals can be used to determine, for example, the mechanical strain along the length of the optical fiber and can ultimately use the determined mechanical strain to determine the shape of the optical fiber. For example, the shape of the segment of fiber may be determined based on the fiber optic signals transmitted to and from the interrogator 126.

In some implementations, the interrogator 126 is an optoelectronic data acquisition system that provides measurements of the light reflected through the optical fiber. The interrogator 126 provides these measurements to the computing device (e.g., the computer system 128) to further determine characteristics of the optical fiber.

In general, a fiber Bragg grating (FBG) is a type of distributed Bragg reflector constructed in a relative short segment of optical fiber that reflects particular wavelengths of light and transmits the light of other wavelengths. An FBG can be produced by creating a periodic variation in the refractive index of a fiber core, which produces a wavelength-specific dielectric mirror. By employing this technique, a FBG can be used as an inline optical fiber for sensing applications. At each periodic refraction change due to the shape of the optical fiber, a small amount of light is reflected. The reflected light signals combine coherently to produce a relatively large reflection at a particular wavelength, e.g., when the grating period is approximately half the input light's wavelength. For example, reflection points can be set up along the optical fiber, e.g., at points corresponding to half wavelengths of the input light. This is referred to as the Bragg condition, and the wavelength at which this reflection occurs is called the Bragg wavelength. Light signals at wavelengths other than the Bragg wavelength, which are Not phase matched, are essentially transparent.

Therefore, light propagates through the grating with negligible attenuation or signal variation. Only those wavelengths that satisfy the Bragg condition are affected and strongly back reflected. The ability to accurately preset and maintain the grating wavelength is one main feature and advantage of Fiber Bragg gratings.

The central wavelength of the reflected component satisfies the Bragg relation: $\lambda_{Bragg}=2$ n$\Lambda$, with n being the index of refraction and $\Lambda$ being the period of the index of refraction variation of the FBG. Due to the temperature and strain dependence of the parameters n and $\Lambda$, the wavelength of the reflected component will also change as function of temperature and/or strain. This dependency can be utilized for determining the temperature or strain from the reflected FBG wavelength.

In some implementations, the nano-magnetometer 122 can provide a reference coordinate system 108 for the system 100 that may be aligned to the patient 106, as described above and in conjunction with the field generator 120. The location, orientation, shape, pose, etc., of the guidewire 112 can be defined within the reference coordinate system 108. In this way, the optical fiber can be tracked relative to the patient anatomy.

In some cardiac applications, the shape of the segment of optical fiber can be used to support medical procedures. For example, the shape of the segment of optical fiber can provide information about a transeptal puncture operation in the context of a mitral valve repair/replacement or a catheter across an atrial septum wall for atrial fibrillation treatment. Additionally, the shape of the segment of the optical fiber can be used to cannulate the vessel entering the kidney from the aorta for a stent placement.

Tracking systems are frequently accompanied by computing equipment, such as the computer system 128, which can process and present the measurement data. For example, in a surgical intervention, a surgical tool measured by the tracking system can be visualized with respect to the anatomy marked up with annotations from the pre-operative plan. Another such example may include an X-ray image annotated with live updates from a tracked guidewire.

Medical procedures that are supported by tracking systems frequently make measurements with respect to a reference co-ordinate system attached to the patient. In doing so, medical professionals can visualize and make measurements with respect to the patient anatomy and correct for gross patient movement or motion. In practice, this can be accomplished by affixing a nano-magnetometer 122 to the distal end of the optical fiber and by sensing the shape of the guidewire 112.

The described tracking systems can be advantageous because they do not require line-of-sight to the objects that are being tracked. That is, they do not require a directly unobstructed line between tracked tools and a camera for light to pass. In some implementations, the described systems have improved metal immunity and immunity to electrical interference. That is, they do not require minimal presence of metals and sources of electrical noise in their vicinity to provide consistent tracking performance.

In medical procedure contexts where the approach of a surgical or endoscopic tool can improve patient outcomes, additional intraoperative imaging modalities can be used such as Ultrasound, MRI, or X-rays, to name a few examples. Another advantage of the described tracking systems, e.g., the system 100 of FIG. 1, is that the shape of the surgical/endoscopic tool is not distorted by imaging artifacts. Also, EMT systems do not require direct manual control of an imaging probe by a skilled practitioner to maintain the quality of visualization. Also, the present systems do not expose the patient and medical staff to ionizing radiation. Thus the number of workflow contexts that stand to benefit from this technology is vast, covering a variety of endovascular procedures, electrophysiology, structural heart interventions, peripheral vascular interventions, bronchoscopic interventions, endoscopic procedures, neurosurgical interventions, biopsy needle guidance, percutaneous coronary interventions, transcatheter embolization procedures, pain management procedures, urological interventions, robotic laparoscopic interventions, and others.

There are techniques by which optical transducers built into an optical fiber can produce measurements (for example wavelength) that can be used to estimate characteristic information along the length of the fiber, e.g., pose, shape, location, etc. In some implementations, the optical fiber may be equipped with a series of FBGs, which amount to a periodic change in the refractive index manufactured into the optical fiber. In some implementations, the optical fiber may rely on Rayleigh scattering, which is a natural process arising from microscopic imperfections in the fiber. Techniques using FBG, Rayleigh scattering, both, etc. have the capacity to reflect specific wavelengths of light that may correspond to strain within the fiber, for example. Deformations in the fiber cause these wavelengths to shift, and the wavelength shift can be measured by a system component referred to as an interrogator 126 that measures wavelength shift by using Wavelength-Division Multiplexing (WDM), Optical Frequency-Domain Reflectometry (OFDR), etc.

With Rayleigh scattering, reflected light in the optical fiber is returned to the reference light, where a beat frequency interference occurs. The magnitude of the signal frequency is linear with the position of the reflected light and the shift of the signal spectrum is related to the change of strain and temperature at the position. The light from the source interferes coherently with the light that was emitted a short time before and scattered back from a certain distance along the sensing fiber. If the sweep is linear, the frequency difference between these two light signals is proportional to the propagation time delay along the sensing fiber, and therefore, to distance. This means that the instantaneous beat frequency measured at the detector is mapped to a specific position along the fiber. OFDR operates in the frequency domain (or Fourier domain): an OFDR sensor system tunes a frequency range and receives a frequency response from the optical fiber which is converted into the time/spatial domain by Fourier transform.

In doing so, the characteristics of the fiber can be estimated, for example, by employing one or more artificial intelligence techniques such as a trained machine-learning system. In some examples, the characteristics of the fiber can be estimated using a FOSS system. By affixing a fiber instrumented as such, a sensing/measurement paradigm can be realized for 6DOF tracking systems, enabling the pose, shape, and position measurements along the optical fiber in the coordinate space of the 6DOF tracking system. Additionally, in an optical tracking supported procedure, this can allow one to take pose measurements outside of the measurement volume or line-of-sight of the optical tracking system. In the context of an electromagnetic tracking supported procedure, this can allow one to take various fiber measurements in a region with high metal distortion where electromagnetic sensors would normally perform poorly, or one can use the fiber measurements to correct for electromagnetic/metal distortion.

While FIG. 1 is largely directed to a system 100 that includes nano-magnetometer components, it should be understood that the system 100 can include optical tracking systems that include, for example, one or more cameras, one or more sensors, e.g., 6DOF sensors, and one or more other components.

As described above, the operation of the system 100 can be controlled by a computer system 128. In particular, the computer system 128 can be used to interface with the system 100 and cause the location information of the nano-magnetometer 122 and the segment of optical fiber within the guidewire 112 to be determined to determine various characteristics of the optical fiber.

In some implementations, the system 100 can provide characteristics of the optical fiber using the data provided by the nano-magnetometer 122. The interrogator 126 and the computing system 128 can measure the phases on the reflected light imparted by the nano-magnetometer 122 and infer the strength of the magnetic field from the measured phases. The computing system 128 can provide information indicative of the strength of the measured field to a trained machine-learning model to produce characteristics of the optical fiber. The trained machine-learning model can output, for example, confidences or statistical likelihoods that can infer position, location, and shape information of the optical fiber. The trained machine-learning model can recognize the strength of the magnetic field measured by the nano-magnetometer 122 as an indication of the nano-magnetometer 122's location and can infer other characteristics of the optical fiber, e.g., pose, shape, and position.

Figures 2, 3:
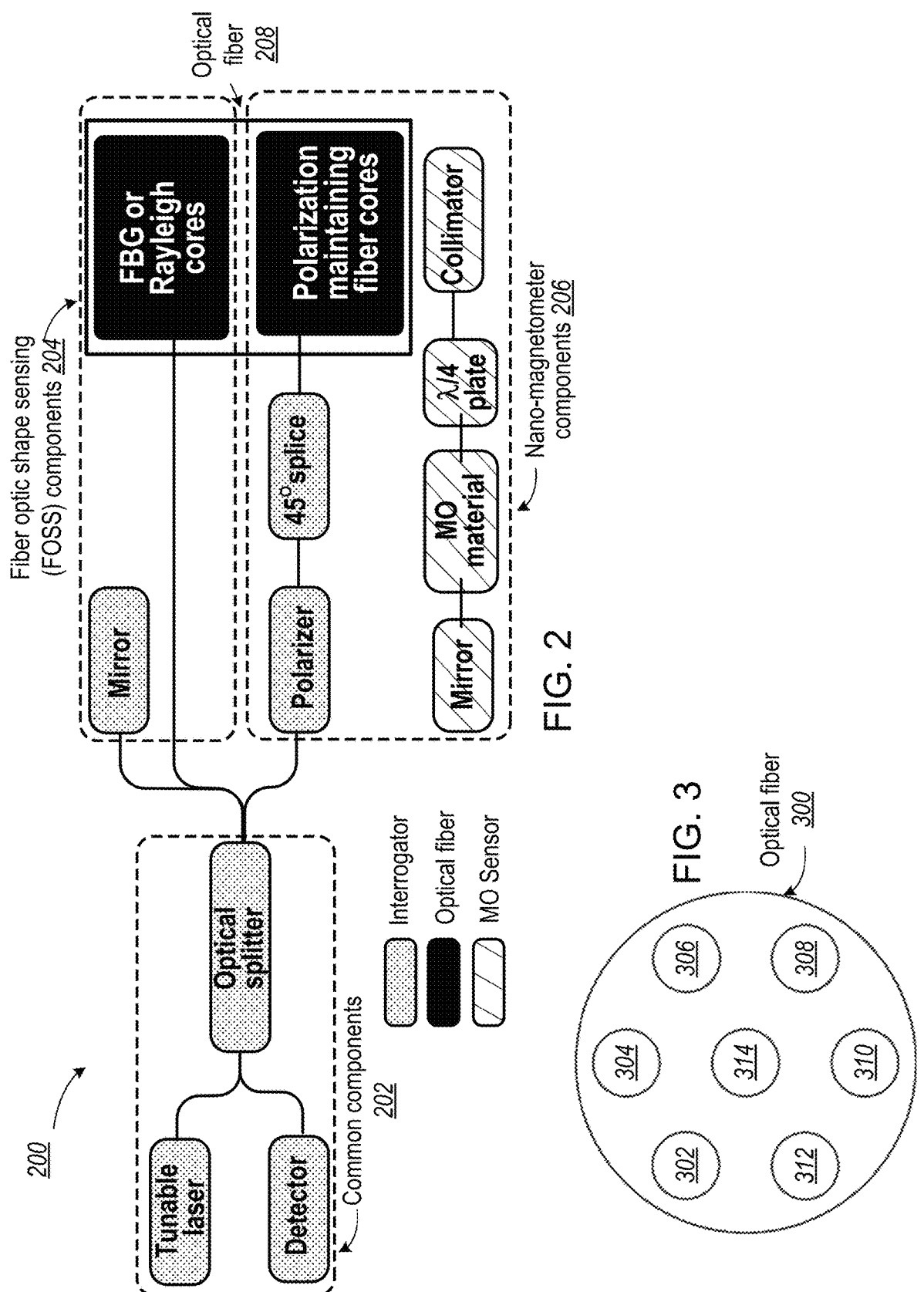
FIG. 2 is a block diagram of an example system for representing one or more components of an optical fiber.
FIG. 3 illustrates an example cross section of an optical fiber.

FIG. 2 is a block diagram of an example system 200 for representing a shape of an optical fiber. The system 200 includes an interrogator, an optical fiber, and a magneto-optic (MO) sensor. As illustrated in system 200, the interrogator can include a tunable laser, a detector, an optical splitter, a polarizer, and 45-degree splicer. The optical fiber can include various components that receive the transmitted light from the interrogator and transmit the reflected light back to the interrogator. Specifically, the optical fiber can include a collimator, λ/4 plate, MO material, and a mirror. The MO sensor can include FBG or Rayleigh cores and polarization maintaining fiber cores.

As illustrated in the example 200, the various components are texture coded to indicate a grouping based on distinct physical components. Similarly, the dotted boxes, e.g., common components 202, fiber optic shape sensing (FOSS) components 204, optical fiber 208, and nano-magnetometer components 206, indicate an association with the distinct measurement technologies. These components of system 200 are similar to the components shown in system 100.

In some implementations, the interrogator can transmit light down the optical fiber and can receive light reflected from the optical fiber. The transmitted light can reflect off the Bragg gratings, the imperfections in the optical fiber, and the nano-magnetometer, and return to the interrogator. Specifically, the returned light reflected off the nano-magnetometer can be phase shifted by an amount that is directly proportional to an amount of magnetic fields sensed by the nano-magnetometer. Here, the nano-magnetometer can impart the phase shift on the light that is directly proportional to the amount of magnetic fields sensed by the nano-magnetometer. The interrogator can be configured to measure the phase shifts in the returned light reflected from the nano-magnetometer to estimate and/or measure the amount of magnetic fields.

In some implementations, the interrogator can measure the phase shift of the received light in various manners. In some examples, the interrogator can utilize a phase locked loop (PLL) that can measure the phase angle between (i) the optical light that was transmitted and (ii) the optical light that was received. In some examples, the interrogator can utilize various demodulation techniques to measure and identify the phase shift. In some examples, the interrogator can calculate or estimate a phase shift of the received light using a phase-contrast microscopy technique. Other techniques to measuring the phase shift of the received light are also possible.

In some implementations, the interrogator can utilize the measured phase shift to estimate the location of the nano-magnetometer. In further detail, the interrogator can determine a strength of the magnetic field sensed by the nano-magnetometer 122 based on an amount of the estimated phase shift measured from the optical light. The strength of the magnetic field can correlate to an amount of estimated phase shift of the optical light. The interrogator can identify the strength of the magnetic field and triangulate, for example, or locate a position of the nano-magnetometer using the strength of the magnetic field.

As shown in FIG. 1, the field generator 120 can emit one or more magnetic fields that are sensed by the nano-magnetometer 122. Each of the one or more magnetic fields can be separated by time, e.g., time division multiplexing, and/or frequency, e.g., frequency division multiplexing, for example. The nano-magnetometer 122 can measure the strength of the emitted magnetic fields at its current location within the patient 106. The strength of the emitted magnetic fields can change as the nano-magnetometer 122 moves throughout the patient 106. Based on the nano-magnetometer 122's measurement of the emitted magnetic fields, the nano-magnetometer 122 can apply a phase shift to the optical light (upon receiving/detecting the optical light) that is proportionate to the strength of the measured emitted magnetic fields. For example, the nano-magnetometer 122 can apply the phase shift to the optical light by shifting the polarized channels before and after they pass through the magneto-optic material and causing interference upon recombination of the channels.

The interrogator can determine the strength of the estimated magnetic fields from the measured phase shift. In some examples, based on the measured phase shift, the interrogator can compare a difference between (i) the amount of power of the magnetic fields emitted by the field generator 120 and (ii) the strength of the magnetic fields determined from the measured phase shift. The interrogator can estimate a pose, for example, of the nano-magnetometer 122 from the location of the field generator 120 using the compared difference. The interrogator can determine that a lower difference indicates the nano-magnetometer is closer to the field generator 120 and likewise, a greater difference, e.g., difference that satisfies a threshold, is farther away from the field generator 120. In response, the interrogator can identify a location of the nano-magnetometer 122 within the patient 106. The location of the nano-magnetometer can be identified, for example, in positional coordinates (X, Y, Z) or other coordinates.

In some cases, the interrogator can determine the location of the nano-magnetometer using the strength of the magnetic fields determined from the measured phase shift. The strength of the magnetic fields can correspond to a particular location above the field generator 120, that indicates to the interrogator an X, Y, Z position of the nano-magnetometer. In some cases, the compared difference between the strength of the magnetic fields emitted by the field generator 120 and the strength of the magnetic fields determined from the measured phase shifts can indicate to the interrogator the X, Y, Z position of the nano-magnetometer. In some examples, the interrogator may access data that correlates the strength of the magnetic field from the field generator 120 to three dimensional locations above the field generator 120. In this manner, the interrogator can reference this stored data in interpreting a location of the nano-magnetometer from a particular strength of the magnetic field from the field generator 120 or a difference in strength of the magnetic field from the field generator 120 and the strength of the magnetic fields from the measured phase shifts.

In some implementations, the system 100 may include multiple field generators 120. Each field generator may be located in different locations underneath the patient 106. In some cases, each field generator can emit a magnetic field with respective characteristics. The respective characteristics can include a particular amplitude, phase, frequency, and polarization. Each field generator can emit the magnetic field with different characteristics, to distinguish a field generator from one another. The nano-magnetometer 122 can impart phase shifts on the reflected light according to the differently emitted magnetic fields and send the corresponding reflected light back to the interrogator 126. The interrogator 126 can interpret each of the different phase shifts from the reflected light to identify the corresponding emitted magnetic fields from the respective field generators. In response, the interrogator 126 can triangulate a location of the nano-magnetometer 122 using the various phase shifts of reflected light. In some cases, the interrogator 126 can triangulate the location of the nano-magnetometer 122 using strengths of the corresponding emitted magnetic fields, transformational matrices for X, Y, and Z locations, and other computational data, for example.

In some examples, the interrogator can utilize a strength of the magnetic fields along with a model of the emitted magnetic fields. Using the model of the emitted magnetic fields, the interrogator can utilize a non-linear system to determine a 5DOF of the nano-magnetometer, the 5DOF describing position and orientation of the nano-magnetometer.

As illustrated in system 200, the common components 202 can include an optical splitter and the nano-magnetometer components 206 can include various components. The nano-magnetometer 206 can use the optical splitter and a polarizer when transmitting reflected phase shifted light down the optical fiber 208. The polarizer is a type of optical filter that allows light waves of a specific polarization to pass through while blocking light waves of other polarizations. The optical splitter can be a device, such as an optical power distribution device, that can split an incident light beam into two or more light beams. Each split light beam can traverse through a particular core of the optical fiber. The core is the physical medium of the fiber that carries the light signal received from an attached light source and delivers it to a receiving device. For example, the fiber core is a continuous hair-thin strand of silica glass or plastic. A cladding can surround the fiber core, and can be a thin layer of glass, which forms a single solid glass fiber that is used for light transmission. The cladding creates a boundary containing the light waves, causing refraction. The coating is designed to absorb shocks, provide protection against excessive cable bends, and reinforce the fiber core. This primary coating is basically a layer of plastic which does not interfere with the cladding or the light transmission of the core. The nano-magnetometer can utilize the optical splitter when transmitting reflected phase-shifted light to the interrogator.

In some implementations, the interrogator can be configured to transmit various wavelengths of light and to measure the various wavelengths of reflected light. Specifically, the interrogator can be modified to extend its dynamic wavelength range that covers the typical operating range of the FOSS system in addition to covering the operating wavelength of the nano-magnetometer. For example, the interrogator can use a light wavelength of 1310 nm.

As illustrated in the example 200, the tunable laser can transmit light down the optical fiber to an optical splitter. The tunable laser can be a 1310 nanometer (nm) laser or another laser with a different wavelength, for example. The optical splitter may be a 2×2 optical splitter, for example. The transmitted light can be passed to a balanced detector in the common components 202 for measurement, to the FBG or Rayleigh cores, and to the polarizer of the nano-magnetometer 206. After the transmitted light passes through the optical splitter, the transmitted light can pass through a polarizer and a 45-degree splicer in the nano-magnetometer components 206. The 45-degree splicer can split the transmitted light equally into the horizontal and vertical axes of the polarization maintaining fiber cores. The horizontal and vertical light are then passed to a collimator. The collimator can narrow a beam of particles or waves. The collimator can be, for example, a graded-index (GRIN) lens. After passing the horizontal and vertical light components through the collimator, the light is passed to a quarter wave plate (QWP or N4 plate). The QWP can convert the two orthogonal polarizations into a right-handed circular polarized (RHCP) light and left-handed circular polarized (LHCP) light.

The RHCP and the LHCP light is then passed to the magneto-optical (MO) material. The back side of the MO film can act as a mirror, which flips the polarization of the RHCP light and the LHCP light by introducing a π phase shift into the light. Thus, the reflected RHCP light and the reflected LHCP light is then passed through the QWP, and the polarization that was traveling in the fast axes of the polarization maintaining fiber cores now moves in the slow axis, and vice versa. When the reflected RHCP light and the reflected LHCP light reach the 45-degree splicer, the reflected lights can re-correlate and combine. Their addition can permit interference between the two orthogonal polarizations. At this point, a faraday rotation inside the nano-composite material creates a phase shift between the two reflected orthogonal polarizations. Due to the design of the nano-magnetometer components 206 and the double pass through the MO material, i.e., once in the forward direction and once when reflected, the phase difference induced by the Faraday rotation can be four times larger than the single pass phase change.

The reflected light is then passed through the optical splitter and provided to the balanced detector of the common components 202. The balanced detector can detect the interference pattern caused by the phase shift induced by a magnetic field between the two polarizations. The balanced detector can determine the phase shift reflective of the interference pattern. The determined phase shift can be provided to the interrogator and the computing system to determine the positional coordinates of the nano-magnetometer from the phase shift.

In some implementations, the nano-magnetometer can be configured using various configurations. In some examples, the nano-magnetometer can be a single component. In some examples, the nano-magnetometer can be implemented as a group of two or more miniaturized nano-magnetometers. These miniaturized nano-magnetometers can each individually communicate with each unused core of three unused cores of the optical fiber. In this example, by utilizing three miniaturized nano-magnetometers, any possible crosstalk at the coupling point between the nano-magnetometer and the optical fiber can be eliminated. In some examples, the three unused cores utilized by the miniaturized nano-magnetometers do not include the Bragg gratings. The remaining four used cores can include the embedded Bragg gratings. In some examples, the nano-magnetometer can be configured to utilize a specific core of the optical fiber to significantly reduce or eliminate the overall crosstalk at the coupling point.

In some examples, the nano-magnetometer can implemented as a group of four miniaturized nano-magnetometers. These miniaturized nano-magnetometers can each individually communicate in a one-to-one match with each core of the four cores of the optical fiber. Specifically, the four miniaturized nano-magnetometers can communicate with the three unused cores and the central core of the optical fiber. Similar to the example above with three miniaturized nano-magnetometers, crosstalk at the coupling point can be eliminated in the example with four miniaturized nano-magnetometers.

In some examples, two more nano-magnetometers may be used to provide a 6DOF electromagnetic tracking solution. In this case, because the MFOS cores are helically wound, multiple nano-magnetometers can be oriented differently from one another. They may have very similar positions within the MFOD, but different orientations due to the helical winding. The two or more orientations can be used to construct, for example, azimuth information, elevation and roll information, while the multiple location solutions can also be provided.

In some implementations, the nano-magnetometer can be designed such that its diameter fits within the diameters of its neighboring components. In further detail, the nano-magnetometer can be designed such that its diameter fits the diameters of various catheters and guidewires, such as those shown in system 100. Moreover, the nano-magnetometer can be designed so that its diameter fits within the diameter of the optical fiber. For example, the diameter of the optical fiber can range between 195 micrometers (μm) and 460 μm.

In some examples, a nano-magnetometer can operate at wavelengths of 1310 nanometers (nm). In order for the nano-magnetometer to operate with the FOSS components, the wavelength of the nano-magnetometer can be shifted to fit within the operating range of the interrogator of the FOSS components. For example, the wavelength of the nano-magnetometer can be increased to 1510 nm to fit within the range of 1510 nm to 1590 nm of the FOSS components. Moreover, by shifting the wavelength of the nano-magnetometer to the lower limit of the range of the interrogator, the nano-magnetometer's operation can match the wavelength distribution of the FOSS components where the lower wavelengths correspond to the distal end of the optical fiber. Similarly, by shifting the wavelength of the nano-magnetometer to the higher limit of the range of the interrogator, the nano-magnetometer's operation can match the wavelength distribution of the FOSS components where the higher wavelengths corresponding to the proximal end of the optical fiber.

The segment of fiber within the guidewire 112 can include multiple components, structures, etc. FIG. 3 illustrates an example cross section of a multiple optical fiber sensor (MFOS) 300. The MFOS 300 can be, e.g., a multi-core fiber optic sensor or multiple, mechanically bundled fiber optic sensors. For example, the MFOS 300 can include multiple cores 302, 304, 306, 308, 310, 312, and 314 (hereinafter "cores 302-314"). A subset of these cores, such as three cores can perform the three-dimensional shape sensing. Lesser degrees of freedom can be determined with fewer fibers. MFOS 300 can include multiple optical cores, each core surrounded by a cladding, and a coating for protection surrounding the entirety of the MFOS 300. The multiple cores 302-314 are the physical medium of the fiber that carries the light signal received from an attached light source, e.g., interrogator 126, and delivers it to a receiving device. For example, the cores 302-314 can be continuous hair-thin strands of silica glass or plastic. The cladding is a thin layer of glass that surrounds each core of the cores 302-314, forming a solid glass fiber that is used for light transmission. The cladding creates a boundary containing the light waves and causing refraction, which enables data to travel the length of the optical fiber. The coating is designed to absorb shocks, provide protection against excessive cable bends, and reinforce the fiber cores 302-314. The coating can be a layer of plastic which does not interfere with the cladding or the light transmission of the cores 302-314.

In some implementations, the optical fibers can include more or fewer components than those shown in the MFOS 300. For example, the MFOS 300 can include multiple fibers with additional strength/position elements. The position elements can maintain a certain geometry and organization of the sensing fibers, and provide additional support to the fibers. In some examples, the MFOS 300 can be further incased in epoxy for strength. For example, the MFOS 300 can be twisted during epoxy bonding resulting in a helical structure. The overall diameter of the MFOS 300 can be larger when the additional strength/position elements are added.

In some implementations, the MFOS 300 can be manufactured using various configurations. As mentioned above, the MFOS 300 can incorporate Bragg gratings and can include multiple cores. In some examples, seven is a common number for a number of cores. The estimation of the optical fiber shape places a requirement of a minimum of three cores spread evenly around the center of the optical fiber. For example, with three cores, each core is positioned at angles of 120 degrees. In some examples, four cores can be incorporated in the MFOS 300, in which each core is positioned at angles of 90 degrees. However, in some cases, when four cores are utilized, the fourth core can be positioned within the center of the optical fiber. The fourth core's position in the center of the optical fiber enables the fourth core to only be affected by temperature, sheer, and tensile strains and not those effects induced from bending. As a result, the core at the center of the optical fiber is used to differentiate between strains induced by bending and strains induced by temperature. This assumes there are no effects caused due to tensile and sheer strains. Additionally, the outer cores of the MFOS 300 may be added to provide structural stability to the optical fiber. As such, in a seven-core configuration of the MFOS 300, three of the outer cores are left unused.

In some implementations, the nano-magnetometer 122 can utilize various cores of the cores of the optical fiber. The nano-magnetometer 122 can transmit the phase-shifted reflected light through the three unused cores of the optical fiber. The three unused cores may be three of the outer cores, for example, such as cores 304, 308, and 312. In some examples, these cores may be designed such that they are equipped with Bragg gratings. In some examples, these cores may be designed without the Bragg gratings, and may instead have microscopic imperfections.

In some implementations, the nano-magnetometer 122 can transmit the phase-shifted reflected light through the central core of the optical fiber. The central core may be core 314 of the optical fiber. By transmitting through the central core, the phase shifted reflected light can be shielded from temperature, sheer, and tensile trains applied to the fiber.

In some implementations, one or more opto-adapters and one or more fan-out splicers can be incorporated into the optical fiber. The opto-adapters and the fan-out splicers can be used to facilitate the coupling between the optical fiber and the nano-magnetometer 122. In further detail, the cores of the optical fiber are split and maintained separately to manage the physical connections The opto-adapters aid in managing the physical connections between the optical fiber and the nano-magnetometer 122. For example, in the case where the nano-magnetometer 122 transmits the reflected phase shifted light through the central core of the optical fiber, the cores of the optical fiber need to be combined at the point of contact with the nano-magnetometer 122.

Figures 4A, 4B:
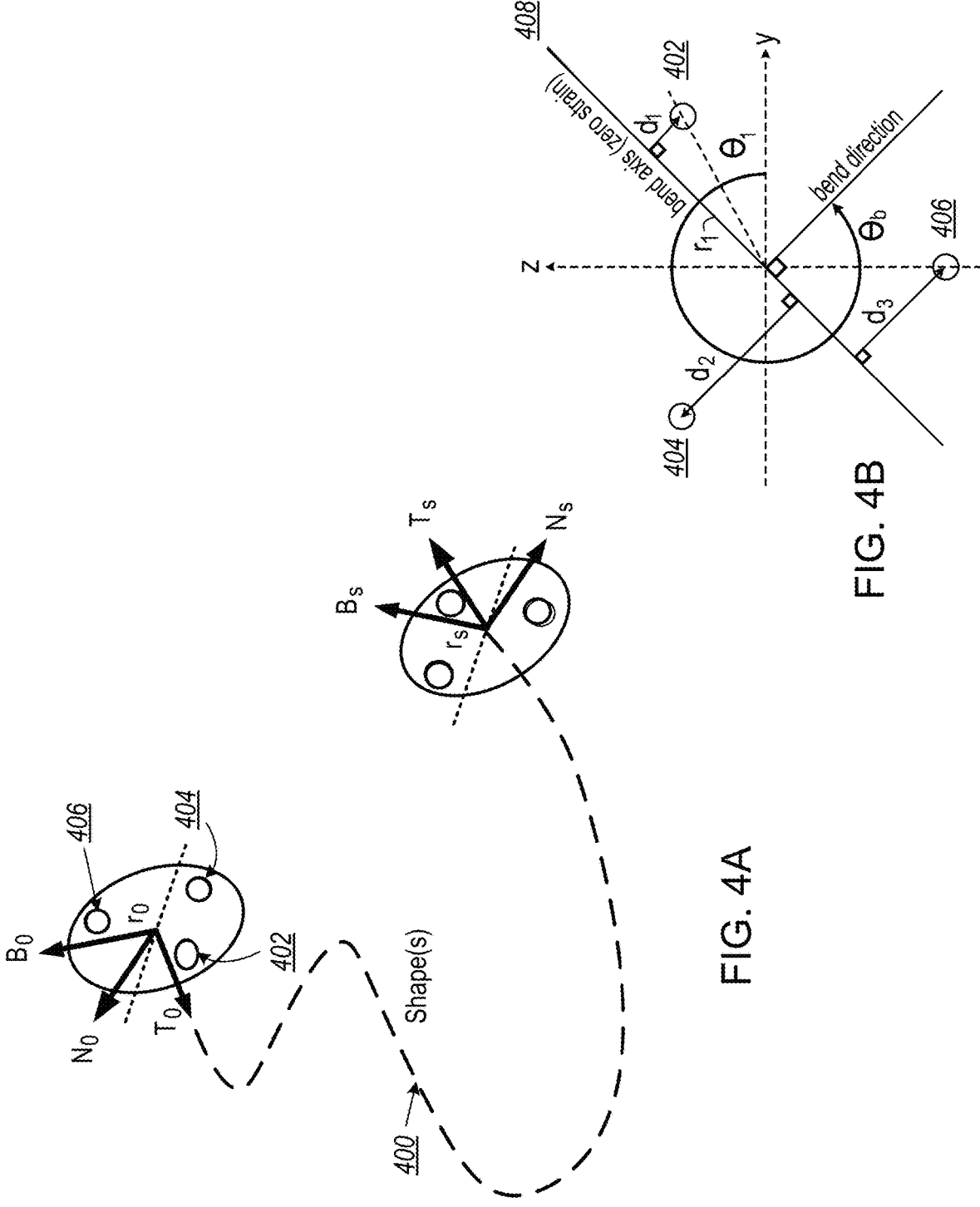
FIGS. 4A-4B illustrate a convention for representing a shape of an optical fiber.

Pose information (e.g., position, orientation, shape) of an optical fiber can be defined, e.g., by a number of functions. FIGS. 4A and 4B illustrate a randomly generated shape 400 of an MFOS. The random 3-D shape is generated as a function of x(s), y(s) and z(s), which together represent the overall shape 400 (e.g., shape(s)) of the MFOS. The random 3-D shape can be used for training a machine-learning model, for example. Once the machine-learning model is sufficiently trained, the trained machine-learning model can be used to compute pose, shape, and/or position information of an optical fiber. The generated shape may have constraints such that the shape represents typical usage scenarios, lengths, tortuosity, etc. When generating the shape 400, initial conditions (e.g., initial location, orientation, etc.) can be set. In the illustrated example, the initial conditions are the initial location and orientation of a first end of the MFOS. Once the shape is fully generated, T(s), N(s) and B(s) are calculated at discrete points s throughout the shape 400. T(s) defines the orientation of the center of the MFOS at each point s. N(s) defines a radial axis of the MFOS, perpendicular to T(s) at each point s. B(s) defines another radial axis of the MFOS, perpendicular to T(s) and N(s) at each point s. T(s), N(s) and B(s) each define a vector and collectively define the orientation of the MFOS at each point s along the shape 400. The number of discrete points s throughout the shape 400 can vary based on requirements for smoothness and are not necessarily equally spaced. Additional fiber cores in the MFOS are generated about the curve of the shape 400. In the illustrated implementation, there are three cores 402, 404, 406. In other implementations, there can be more or fewer fiber cores. By having a core at the center of the shape 400, the system can differentiate various characteristics from one another, e.g., strain from temperature. In some implementations, there can be a core at the center of the shape 400.

The generation of the additional cores is performed by forming a curve for the core as a function of s and t, where s parametrizes the length of the core and t parameterizes the orientation of the core. Each additional core has a respective curve. For example, with three cores 402, 404, 406, there are three additional curves. Assuming the cores are evenly spaced around a circle of radius r, where r, is the radial distance of each core from the center of the shape, the location of each core relative to the center of the shape 400 can be determined from equation (1). In this example, t could be three values to evenly space the cores (e.g., 0, $2\pi/3$, $4\pi/3$). As discussed above, the shape 400 is comprised of three components, x(s), y(s) and z(s) and there are also three components each of T(s), N(s), and B(s).

$$\text{Curve}(s, t) = \text{shape}(s) + N(s)r\cos(t) + B(s)r\sin(t) \qquad (1)$$

With the cores generated about the center of the shape 400, the angles and distances of the cores relative to the center of the shape 400 can be determined at each point s along the shape 400. With additional reference to FIG. 4B, the angle $\Theta_1$ and distances $r_1$ and $d_1$ can be calculated for the angle and distance of the first core 402 from the center of the MFOS. The angle $\Theta_1$ and radius $r_1$ can act as polar coordinates to define the position of the core relative to the center of the MFOS. The bend axis angle $\Theta_b$ can define the direction of a bend in the MFOS. A bend axis 408 is perpendicular from the bend axis angle $\Theta_b$. The distance $d_1$ defines the distance of the first core 402 from the bend axis angle 408.

Once the angle and distance of each core relative to the shape 400 is determined, e.g., at each point s along the shape 400, the curvature κ of each individual cores 402, 404, 406 can be determined at each point s along the shape 400. The curvature κ is determined by calculating for each core curve.

$$\kappa_i(s) = \left\| T_i'(s) \right\| \tag{2}$$

Once information regarding κ and d is determined, e.g., relative to the shape 400, the strain &, e.g., due to twisting and bending, on each core can be determined. This information can be used as training data, for example. As further defined below with respect to FIGS. 5 and 6, this training data can be used to train a machine-learning model.

Figure 5:
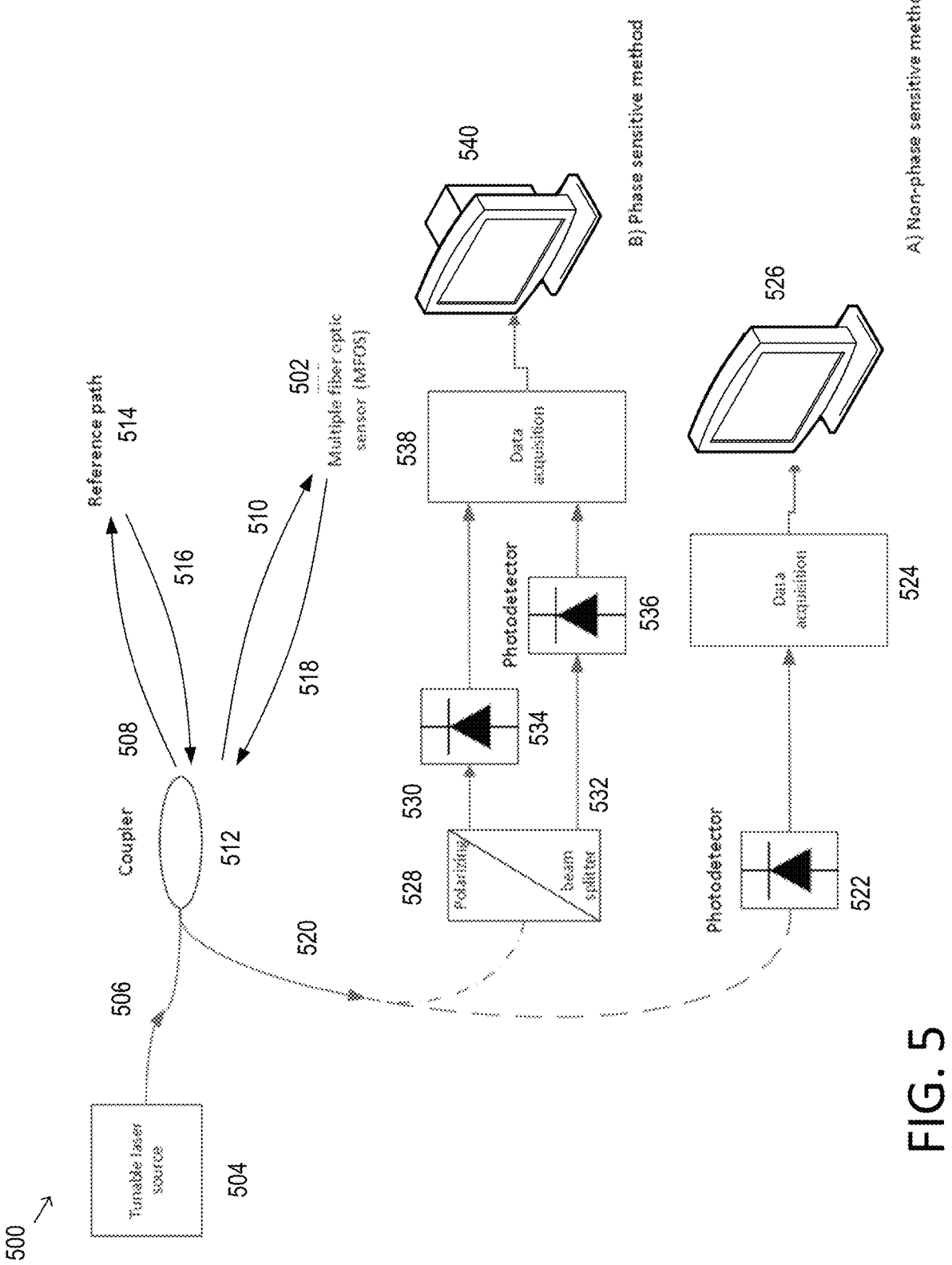
FIG. 5 shows a data flow diagram that graphically represents collecting characteristics of an optical fiber.

FIG. 5 illustrates a block diagram for collecting characteristics in an optical fiber graphically represents a Fiber Optic Shape Sensing (FOSS) system 500 that utilizes Optical Frequency Domain Reflectometry (OFDR) and an MFOS 502. A tunable laser source 504 is linearly swept over a limited range of wavelengths, e.g., about 1-1.5 μm. A light 506 emitted by the laser source 504 is divided into two beams 508 and 510 by optical coupler 512. The beam 508 follows a reference light path 514 and is fixed by design. The reference light path 514 receives beam 508 and returns beam 516. The second beam 510 is sent into the MFOS 502 and the MFOS returns beam 518, which carries information related to the strain in the MFOS 502. The returning beams 516 and 518 cause interference patterns to occur in coupler 512. These interference patterns are represented in a beam 520.

The beam 520 containing the interference patterns can be analyzed through a variety of methods. For example, the beam 520 can be analyzed for amplitude information, which is not phase sensitive. In this case, the interference represented in the beam 520 is measured by a photodetector 522. The photodetector 522 converts light into electrical signals that are then processed by a data acquisition system 524. The data acquisition system 524 can include, e.g., one or more analog to digital (A/D) converters. One or more other signal processing techniques may also be employed in the data acquisition system 524 (e.g., filtering, etc.). The data processed by the data acquisition system 524 can be provided (e.g., uploaded) to a computer system 526. The computer system 526 can be trained by a machine-learning (ML) process, where the data from the data acquisition system 524 can be converted into a shape of the MFOS 502. In some implementations, the computer system 526 can determine the shape of the MFOS 502 using other calculation processes with the data processed by the data acquisition system 524.

Another technique of analyzing the beam 520 containing the interference patterns is analyzing both amplitude and phase information, e.g., a phase sensitive technique. For example, the beam 520 can be split into, e.g., orthogonal polarizations by a photodetector 528. For example, polarization component 530 refers to the component of the beam 520 perpendicular to the incident plane, while polarization component 532 refers to the component of the beam 520 in the plane. Each component is measured by a respective photodetectors 534, 536, which convert the respective light into electrical signals that are then processed by a data acquisition system 538. The data acquisition system 538 can include, e.g., one or more A/D converters and potentially components to perform one or more other signal processing techniques (e.g., filtering). The converted signals from the data acquisition system 538 can be provided (e.g., uploaded) to a computer system 540. The computer system 540 can be trained by a machine-learning (ML) process, where the data from the data acquisition system 538 can be converted into a shape of the MFOS 502.

Figure 6:
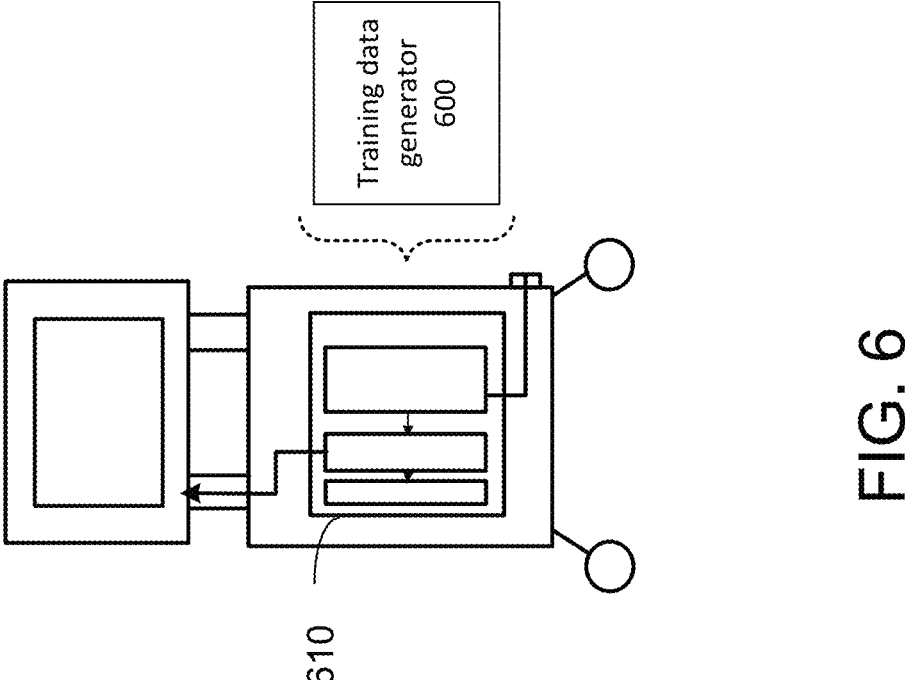
FIG. 6 is a computer system executing a training data generator that collects training data to train an optical fiber characteristic sensing machine-learning system.

The computer systems (e.g., computer 526, 540) described can execute a training data generator, which utilizes the captured data to determine a position and orientation of a surgical tool (or other object). Referring to FIG. 6, a computer system 610 executes a training data generator 600. The computer system 610 can be similar to the computer system 128 of FIG. 1. The training data generator 600 (e.g., a program, software, software application, or code) includes machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

Figure 7:
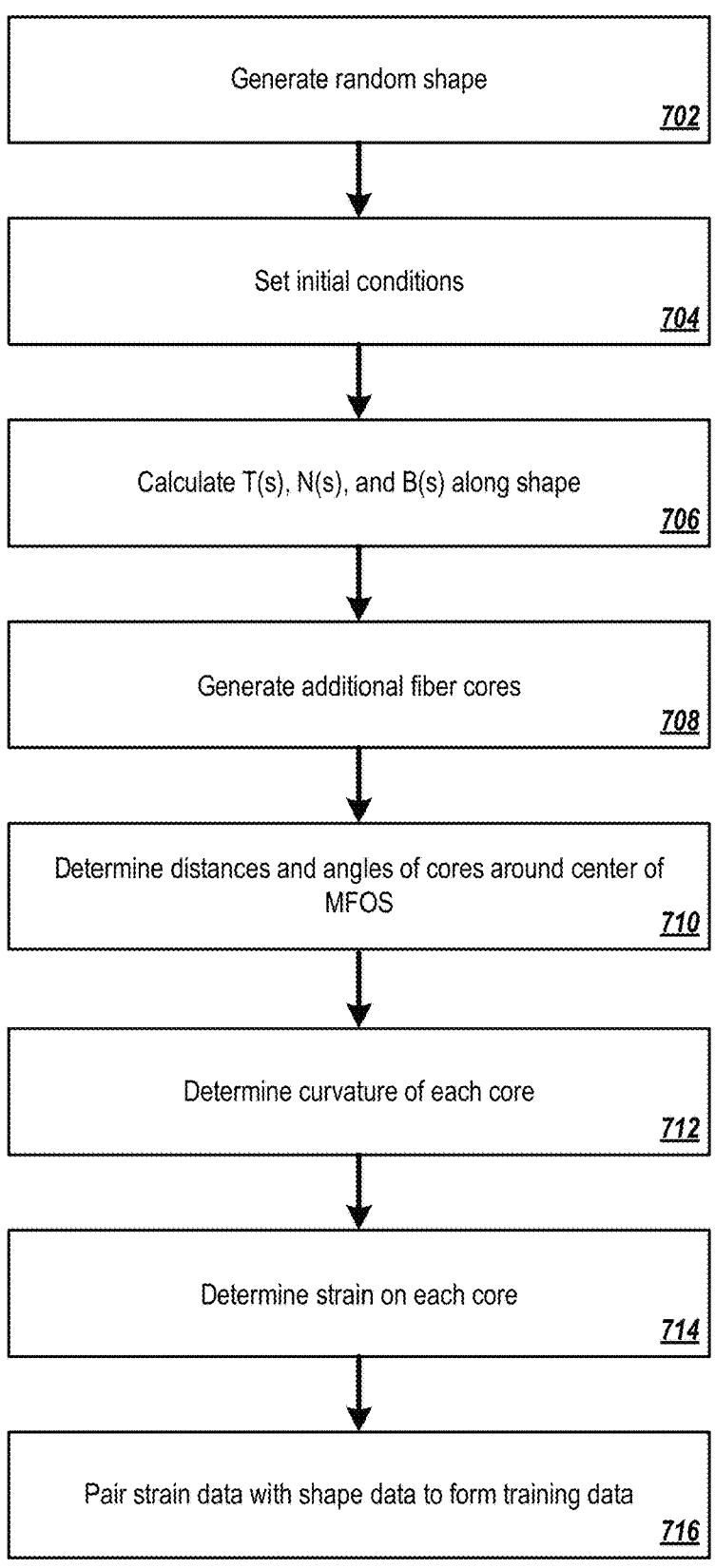
FIG. 7 is a flowchart of operations of a training data generator to computationally generate training data to train an optical fiber characteristic sensing machine-learning system.

FIG. 7 is a flowchart of a method 700 for computationally generating data to train a machine-learning system to determine a shape of an MFOS. For example, operations of a training data generator (e.g., the training data generator 600 of FIG. 6) can follow the method 700. First, a random 3-D shape is generated (702). For example, the random 3-D shape can be generated as a function of x(s), y(s), and z(s) to represent the overall generated shape. The random 3-D shape can be generated using the process described with respect to FIGS. 4A and 4B, for example. The generated shape may have constraints such that the shape represents typical usage scenarios, lengths, tortuosity, etc., as described above.

Next, initial conditions for the generated shape can be set (704). For example, the initial conditions can include an initial location and orientation of a first end of the shape. Other initial conditions can also be set (e.g., N(0), B(0)).

Then, T(s), N(s), and B(s) can calculated at discrete points s throughout the generated shape (706). T(s) defines the orientation of the center of the shape at each point s. N(s) defines a radial axis of the shape, perpendicular to T(s) at each point s. B(s) defines another radial axis of the shape, perpendicular to T(s) and N(s) at each point s. T(s), N(s) and B(s) define the area of the shape at each point s along the generated shape. The number of discrete points s throughout the shape can vary based on requirements for smoothness and are not necessarily equally spaced.

Next, additional fiber cores are generated about the curve of the shape (708). For example, there can be three cores. In other implementations, there can be more or fewer fiber cores. In some implementations, there can be a core at the center of the shape. The generation of the additional cores can be performed, e.g., by forming a curve for the core as a function of s and t, where s parametrizes the length of the core and t parameterizes the orientation of the core. Each additional core can have a respective curve. For example, with three cores, there can be three additional curves. Assuming the cores are evenly spaced around a circle of radius r, where r, is the radial distance of each core from the center of the shape, the location of each core relative to the center of the shape can be determined as described above.

Then, the angles and distances of the cores relative to the center of the shape can be determined at discrete points s along the shape (710). For example, an angle ⊖ and distances r and d can be calculated for the angle and distance of a core from the center of the shape, as described above. The angle ⊖ and radius r can act as polar coordinates to define the position of the core relative to the center of the shape. A bend axis angle ⊖$_b$ can define the direction of a bend in the shape at point s.

Next, the curvature κ of each individual cores can be determined (712). For example, the curvature of each individual core can be determined for each point s along the shape, as described above.

Then, the strain ε on each core can be determined (714). For example, the strain can be due to twisting and bending. The strain ε can be determined at each point s along the shape. The strain data can be represented as, e.g., vectors or matrices.

The strain ε on each core and the randomly generated shape can then be used as ML training data. For example, the random shape and the strain data can be paired (716), and the ML training data can be used to train a machine-learning system to determine the randomly generated shape from the strain data. For example, the method 700 can be repeated as necessary to generate enough data to train the machine-learning system. The machine-learning system can be trained to receive core strains as input and output the shape of the MFOS.

To implement the machine-learning system, one or more machine-learning techniques may be employed. For example, supervised learning techniques may be implemented in which training is based on a desired output that is known for an input. Supervised learning can be considered an attempt to map inputs to outputs and then estimate outputs for previously unseen inputs (a newly introduced input). Unsupervised learning techniques may also be employed in which training is provided from known inputs but unknown outputs. Reinforcement learning techniques may also be used in which the system can be considered as learning from consequences of actions taken (e.g., inputs values are known and feedback provides a performance measure). In some arrangements, the implemented technique may employ two or more of these methodologies.

In some implementations, neural network techniques may be implemented using the data representing the strain (e.g., a matrix of numerical values that represent strain values at each point s along a shape) to invoke training algorithms for automatically learning the shape and related information. Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to training data. By using the strain data (e.g., vectors or matrices), a function may be defined that quantifies error (e.g., a squared error function used in regression techniques). By minimizing error, a neural network may be developed that is capable of determining attributes for an input image. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implemented to reduce its effects.

One type of machine-learning referred to as deep learning may be utilized in which a set of algorithms attempt to model high-level abstractions in data by using model architectures, with complex structures or otherwise, composed of multiple non-linear transformations. Such deep learning techniques can be considered as being based on learning representations of data. In general, deep learning techniques can be considered as using a cascade of many layers of nonlinear processing units for feature extraction and transformation. The next layer uses the output from the previous layer as input. The algorithms may be supervised, unsupervised, combinations of supervised and unsupervised, etc. The techniques are based on the learning of multiple levels of features or representations of the data (e.g., strain data). As such, multiple layers of nonlinear processing units along with supervised or unsupervised learning of representations can be employed at each layer, with the layers forming a hierarchy from low-level to high-level features. By employing such layers, a number of parameterized transformations are used as data propagates from the input layer to the output layer. In one arrangement, the machine-learning system uses a fifty-layer deep neutral network architecture (e.g., a Res-Net50 architecture).

The machine-learning system can be, e.g., a neural network. Additionally, multiple smaller neural networks may be put together sequentially to accomplish what a single large neural network does. This allows partitioning of neural network functions along the major FOSS technology blocks, strain measurement, bend and twist calculations, shape calculations, and position calculations. For example, a neural network can act as a Fourier Transformer. In some implementations, training smaller networks may be more efficient. For example, determining regression models on smaller chunks of data may be more efficient than determining models on larger sets of data.

FIG. 8 is a flowchart of a method 800 for physically generating data to train a machine-learning system to determine characteristics of an MFOS. These characteristics can include, for example, shape, position, location, and other characteristics. For example, operations of a training data generator (e.g., the training data generator 600 of FIG. 6) can perform the method 800. In the method 800, rather than using simulated shapes, a training MFOS is set into a certain shape and the resulting strained are measured, e.g., using system 500 as described above.

First, a random shape is generated (802). For example, the random 3-D shape can be generated as a function of x(s), y(s), and z(s) to represent the overall generated shape. This can be performed using the processes described with respect to FIGS. 4A and 4B, for example. The generated shape may have constraints such that the shape represents typical usage scenarios, lengths, tortuosity, etc., as described above.

Next, a physical MFOS is positioned in the random generated shape (804). For example, a robotic MFOS can position itself into the random generated shape. In another example, a user can position the MFOS into the generated shape.

Then, the shape of the MFOS can be measured (806). For example, the shape of the MFOS can be measured, e.g., using a calibrating system. Measuring the shape of the MFOS using hardware equipment can improve the training data. For example, the shape of the MFOS may not be exact to the randomly simulated shape. Also, the measurements of the shape may not be exact, e.g., due to manufacturing tolerances. Along with collecting training data, the method 800 can be used to calibrate a system, e.g., similar to system 500. In some examples, the position of the MFOS, the location of the MFOS, and/or other data related to the MFOS can be measured and used for the ML training data, depending on the context of the training of the ML training data.

Next, the strain in the MFOS can be measured (808). For example, the strain in the MFOS can be measured with a system similar to system 500. The strain ε can be measured at discrete points s along the shape. The strain and the measured shape can then be used as ML training data. For example, the random shape and the strain data can be paired (810), and the ML training data can be used to train a machine-learning system to determine the randomly generated shape from the strain data. The method 800 can be repeated as necessary to generate enough data to train the machine-learning system. The machine-learning system can be trained to receive strain data as input and output the shape of the MFOS. For example, the machine-learning system can be trained similarly to the machine-learning system 610, as described above. The position, shape, and/or location of the MFOS can also be measured and used as ML training data.

The training data collected by the methods described above (e.g., by the training data generator 600) can be used to train a machine-learning system. For example, one or more techniques may be implemented to determine shape information based on provided strains to a computer system (e.g., the computer system 128). For such techniques, information may be used from one or more data sources. For example, data (e.g., strain data) may be generated that represents the strain throughout an optical fiber. For one type of data collection method, training data can be generated using simulated shapes (e.g., similar to the method 700 of FIG. 7).

Along with the simulated shapes, other techniques may be used in concert for determining shape information. One or more forms of artificial intelligence, such as machine-learning, can be employed such that a computing process or device may learn to determine shape information from training data, without being explicitly programmed for the task. Using this training data, machine-learning may employ techniques such as regression to estimate shape information. To produce such estimates, one or more quantities may be defined as a measure of shape information. For example, the level of strain in two locations may be defined. One or more conventions may be utilized to define such strains. Upon being trained, a learning machine may be capable of outputting a numerical value that represents the shape between two locations. Input to the trained learning machine may take one or more forms. For example, representations of strain data may be provided to the trained learning machine. One type of representation may be phase sensitive representations of the strain data (e.g., containing both amplitude and phase information, similar to FIG. 5). Another type of representation may be non-phase sensitive representations of the strain data (e.g., containing only amplitude information). In some arrangements, a machine-learning system may be capable of rendering imagery from provided input. Once rendered, the imagery may be used to determine a shape of the optical fiber. The machine-learning system may also be capable of rendering one or more components (e.g., x(s), y(s), and z(s)) from the provided input. Once rendered, the components can define the shape of the optical fiber, e.g., in an axis.

To implement such an environment, one or more machine-learning techniques may be employed. For example, supervised learning techniques may be implemented in which training is based on a desired output that is known for an input. Supervised learning can be considered an attempt to map inputs to outputs and then estimate outputs for previously unused inputs. Unsupervised learning techniques may also be used in which training is provided from known inputs but unknown outputs. Reinforcement learning techniques may also be employed in which the system can be considered as learning from consequences of actions taken (e.g., inputs values are known and feedback provides a performance measure). In some arrangements, the implemented technique may employ two or more of these methodologies. For example, the learning applied can be considered as not exactly supervised learning since the shape can be considered unknown prior to executing computations. While the shape is unknown, the implemented techniques can check the strain data in concert with the collected shape data (e.g., in which a simulated shape is connected to certain strain data). By using both information sources regarding shape information, reinforcement learning techniques can be considered as being implemented.

In some arrangements, neural network techniques may be implemented using the training data as well as shape data (e.g., vectors of numerical values that represent shapes) to invoke training algorithms for automatically learning the shapes and related information, such as strain data. Such neural networks typically employ a number of layers. Once the layers and number of units for each layer are defined, weights and thresholds of the neural network are typically set to minimize the prediction error through training of the network. Such techniques for minimizing error can be considered as fitting a model (represented by the network) to the training data. By using the shape data and the strain data, a function may be defined that quantifies error (e.g., a squared error function used in regression techniques). By minimizing error, a neural network may be developed that is capable of estimating shape information. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implements to reduce its effects.

Figure 9:
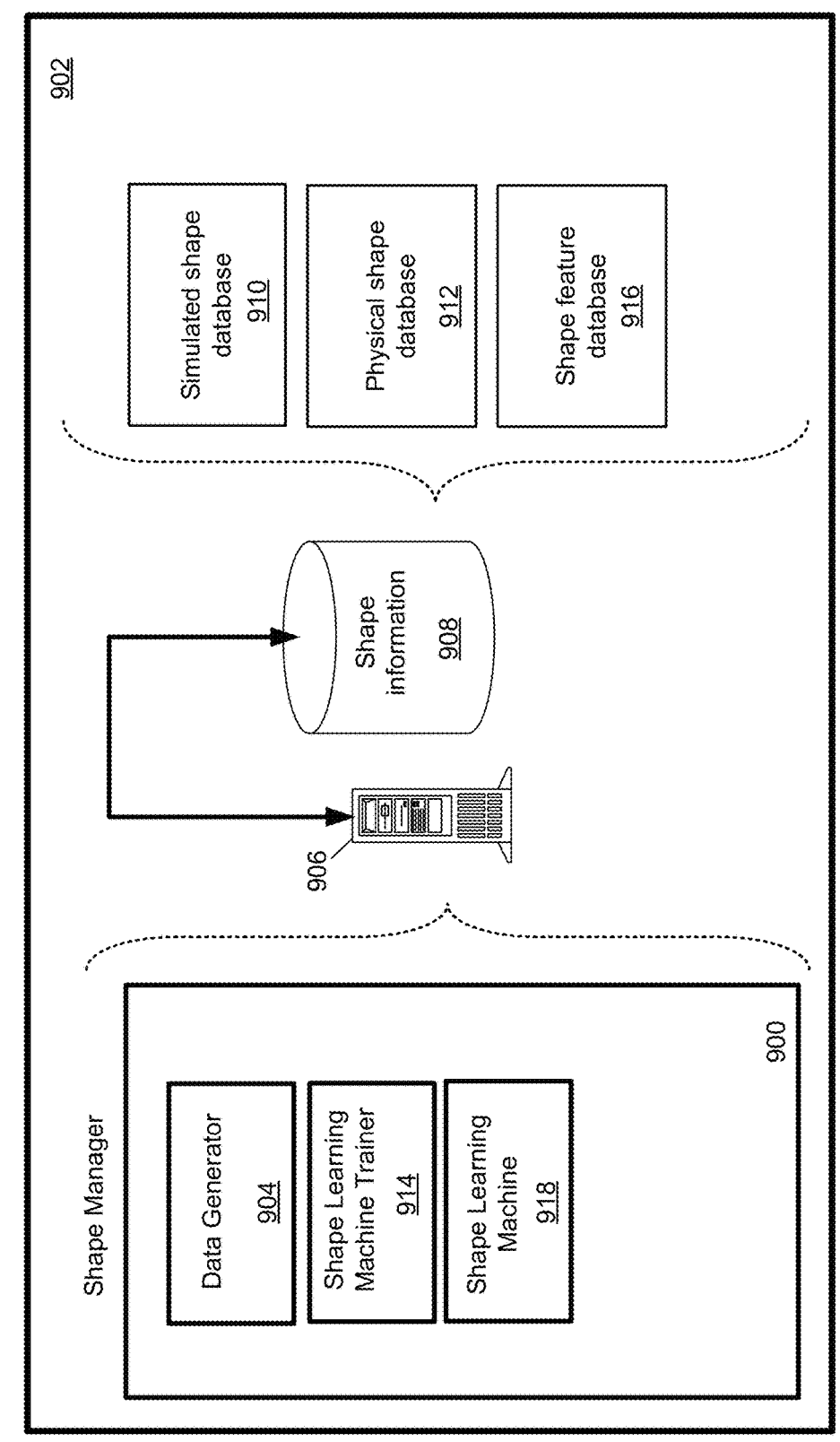
FIG. 9 is a computational system that determines characteristic information of an optical fiber.

Illustrated in FIG. 9, the shape manager 900 (which includes a number of modules) is executed by the server 906 present at a computational environment 902. In this arrangement, the shape manager 900 includes a data generator 904, which can collect training data. In this arrangement, such data may be previously stored (e.g., in a strain database) and retrieved from the storage device 908. Data representing such shape information may also be retrieved from one or more sources external to the computational environment 902; for example, such information may be attained from one or more storage devices of a shape manager (e.g., an entity separate from the computational environment 902). Along with strain data, the storage device 908 (or other storage devices at the computational environment 902) may contain databases of shapes. For example, the storage device 908 contains a simulated shape database 910 containing shape data which is computationally generated (e.g., generated by the method of FIG. 7) and a physical shape database 912 containing shape data that is physically generated (e.g., generated by the method of FIG. 8). A shape database can include information about numerous previously determined shapes, newly determined shapes, etc. From the information stored in the shape databases 910, 912, data may be retrieved for learning machine training and use, e.g., to determine shape information (e.g., the shape of an optical fiber, etc.). For example, the shape databases 910, 912 may include data that represents various types of shape information (e.g., rendered shapes, components in the x, y, and z axis, etc.)

To train a learning machine (e.g., implemented as a neural network), the shape manager 900 includes a shape learning machine trainer 914 that employs both simulated shapes and physical shapes for training operations. In some arrangements, the trainer 914 may calculate numerical representations of strain data (e.g., in vector form) for machine training.

As illustrated in FIG. 9, the shape learning machine trainer 914 may also provide other types of functionality. For example, the shape learning machine trainer 914 may store shape features (e.g., calculated feature vectors) in a shape feature database 916 for later retrieval and use. Such shape feature data may be attained from sources other than the shape learning machine trainer 914. For example, the shape learning machine 918 may similarly store data representing shape features in the shape feature database 916. In some arrangements, such shape features may be directly provided to the shape learning machine trainer 914, the shape learning machine 918, etc. and correspondingly stored in the shape feature database 916. In other arrangements, calculations may be executed by the shape learning machine trainer 914, the shape learning machine 918, etc. to produce the shape features prior to being stored in the shape feature database 916. For example, numerical values representing one or more shape features (e.g., feature vectors) may be computed from strain data by the shape learning machine trainer 914, the shape learning machine 918, etc. As illustrated in the figure, such stored shape feature data may reside in the storage device 908 (e.g., in the shape feature database 916). Such shape feature data may be provided to or received from other locations internal or external to the computational environment 902. For example, the data may be provided for further analysis, storage, etc. to other systems remotely located from the computational environment 902.

In general, the shape learning machine trainer 914 may employ one or more techniques to produce the shape learning machine 918 (e.g., a neural network). For example, the strain data for each shape in the shape databases may be used to define a function. By determining a shape from the provided strain data, the shape learning machine 918 may be trained.

Once trained, the shape learning machine 918 may be used to determine the shape of an optical fiber based on strain data (not used to train the machine). For example, strain data may be provided to the shape learning machine 918. For example, numerical representations (e.g., vectors) of the strain data may be input and the shape learning machine 918 may calculate a shape components for the optical fiber (e.g., components x(s), y(s), and z(s) of the shape). From the calculated shape components, the shape learning machine 918 can render a 3D representation of the shape.

In the illustrated example shown in FIG. 9, the functionality of the data generator 904, the shape learning machine trainer 914, and the shape learning machine 918 are presented as being included in the shape manager 900. However, in some arrangements, the functionality of one or more of these modules may be provided external from the computational environment 902. Similarly, the simulated shape database 910, physical shape database 912, and shape feature database 916 are stored in the storage device 908 in this example. However, one or more of these databases may be stored external to the storage device 908 and in some arrangements one or more of the databases may be stored external to the computational environment 902. In some arrangements, the shape manager 900 may be implemented in software, hardware, or combinations of hardware and software. Similarly the modules included in the shape manager 900 may individually be implemented in hardware and/or software. One or more database techniques (e.g., structural representations, etc.) may be employed for storing the databases 910, 912, 916.

Figure 10:
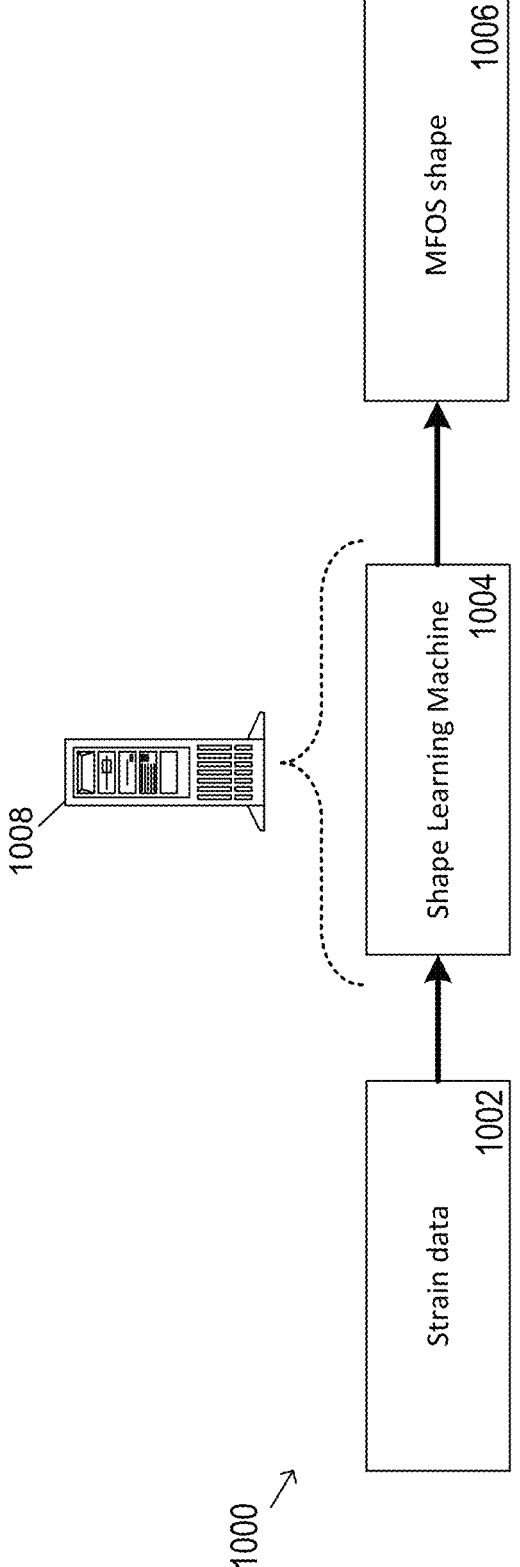
FIG. 10 is a data flow of operations of an optical fiber characteristic learning machine.

FIG. 10 is a data flow for a method 1000 representing operation of a shape learning machine after being initially trained. As described above, training data can be employed from a number of sources; for example, simulated shapes (e.g., such as data generated from a method such as method 700 shown in FIG. 7), physical shapes (e.g., such as data generated from a method such as method 800 shown in FIG. 8), both simulated shapes and a physical MFOS, etc. can be used to generate the training data. Strain data 1002 can be provided to the shape learning machine 1004, which is run within a computer system 1008. The shape learning machine 1004 can determine a shape from the strain data. FIG. 10 represents strain data 1002 being input into the shape learning machine 1004 and producing an output 1006 that represents how the MFOS is shaped. In some arrangements, additional information may also be entered into the shape learning machine 1004, such as initial conditions. The output 1006 can include a function of x(s), y(s) and z(s). Also, a value that represents a confidence level may be output for each of the functions (e.g., ranging from a level of 0.0 to 1.0). In some arrangements, the output 1006 can be a 3-D rendering of an MFOS. In some examples, the shape learning machine 1004 can be configured to produce position and/or pose information of the MFOS.

FIG. 11 is a flowchart 1100 of determining a shape of an optical fiber. The flowchart 1100 can typically be executed by a single computing device, e.g., computing system 128. However, multiple computing devices, e.g., the interrogator 126, the control unit 116, the sensor interface unit 118, and the computing system 128, among others, can execute the processes illustrated by flowchart 1100. Along with being executed at a single site, the execution of flowchart 1100 may be distributed among two or more locations over a network.

The computing device can obtain optical signals reflected through a fiber, the fiber can include one or more embedded sensors and a nano-magnetometer embedded at a distal location of the fiber (1102). The computing device can instruct a tunable laser to transmit the optical signals through the fiber, the optical signals including light that has a range of wavelengths. The one or more embedded sensors can include one or more Fiber Bragg gratings embedded at various locations along the fiber. The Bragg gratings can be designed and/or configured to reflect a specific wavelength, known as a Bragg wavelength, e.g., a frequency shift. The Bragg wavelength can be a function of the strain of the optical fiber. The nano-magnetometer can embedded at a distal end of the fiber. The fiber can include multiple cores.

The nano-magnetometer can reflect a portion of the optical signals through a first subset of the cores and the Bragg gratings can reflect a portion of the optical signals through a second subset of the cores, the first subset of the cores being different from the second subset of cores. For example, cores 314, 304, 308, and 312 can be used for shape sensing and cores 306, 302, and 310 can be used for communications caused by the nano-magnetometer, e.g., magnetic tracking.

The computing device can determine a frequency shift of each of the reflected optical signals, the frequency shift imparted on the reflected optical signals by the one or more embedded sensors (1104). Specifically, the computing device can determine a measure of bend at various location along the fiber using the determined frequency shift of each of the reflected optical signals. As mentioned above, when transmitted light reflects off a Bragg grating, the Bragg grating is configured to reflect a specific wavelength. This specific wavelength is a function of the strain of the optical fiber. The interrogator can receive the reflected optical signals from the optical fiber and the interrogator can measure the frequency shift of each of the reflected optical signals by comparing the specified wavelength, e.g., the Bragg wavelength, to the wavelength of the transmitted light.

The computing device can determine a phase shift of each of the reflected optical signals, the phase shift imparted on the reflected optical signals by the nano-magnetometer (1106). In response to the interrogator receiving the reflected optical signals from the optical fiber, the interrogator can measure the phase shift of each of the reflected optical signals. The interrogator can provide the estimated phase shift of each of the reflected optical signals to the computing system. The computing system can determine one or more magnetic fields sensed by the nano-magnetometer from the determined phase shift of each of the reflected optical signals. Based on the one or more determined magnetic fields, the computing system can identify a location of the nano-magnetometer at the distal location of the fiber in the patient. The location can be utilized as the external reference for the location of the fiber.

The computing device can determine one or more characteristics of the fiber using the determined frequency and the phase shift of each of the reflected optical signals (1108). The one or more characteristics of the fiber includes a shape of the fiber and a location of the fiber in relation to an external reference. In response to measuring the estimated frequency shift and the estimated phase shift of the reflected optical signals, the computing device can determine various characteristics of the fiber. For example, the estimated frequency shift can indicate to the computing device a measure of bend at various locations along the fiber. Specifically, the determined frequency shift can indicate a location of the strain of the fiber and a location of each of the one or more embedded sensors in the fiber. The computing device can determine the location of each of the measured strains of the fiber by correlating the determined frequency shifts to the determined location of each of the one or more embedded sensors.

Moreover, based on the determined strains at each of their respective locations on the fiber, the computing system can estimate a shape of the fiber. The shape of the fiber can be estimated by combining, at each location of the strain, the curvature of the fiber and the angle of the curvature. For each, the curvature of the fiber and the angle of the curvature can be determined based on the determined strain at each of the locations indicated by the Bragg gratings. The estimated shape of the fiber can indicate a shape of the fiber in three-dimensional spatial coordinates. And, the estimated shape of the fiber can include an orientation of a center of the fiber, a first radial axis of the fiber, and a second radial axis of the fiber. Other characteristics of the fiber can also be determined.

For example, in response to estimating the shape of the fiber, the computing device can determine the location of the fiber in the patient. The location of the fiber can be determined using the estimated shape of the fiber and the identified location of the nano-magnetometer, which represents the external reference and aids in overall location identification of the optical fiber.

In some implementations, a machine-learning model can be trained to predict the one or more characteristics of the fiber. The machine-learning model can be trained using various data types, e.g., simulated data, physical data, estimated frequency shifts, estimated phase shifts, strain estimations, curvature of the fiber, and other characteristics. Once the model is sufficiently trained, the trained machine-learning model can be deployed and used at the computing system to aid in the determination of the location of the optical fiber.

Figure 12:
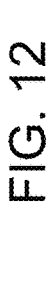
FIG. 12 shows a block diagram of a computing system that can be used in connection with methods described in this document.

FIG. 12 is a block diagram of computing devices 1200, 1250 that may be used to implement the systems and methods described in this document, as either a client or as a server or multiple servers. Computing device 1200 and 1250 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations, e.g., as a server bank, a group of blade servers, or a multi-processor system.

The memory 1204 stores information within the computing device 1200. In one implementation, the memory 1204 is a computer-readable medium. In one implementation, the memory 1204 is a volatile memory unit or units. In another implementation, the memory 1204 is a non-volatile memory unit or units.

The storage device 1206 is capable of providing mass storage for the computing device 1200. In one implementation, the storage device 1206 is a computer-readable medium. In various different implementations, the storage device 1206 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 1204, the storage device 1206, or memory on processor 1202.

The high-speed controller 1208 manages bandwidth-intensive operations for the computing device 1200, while the low speed controller 1212 manages lower bandwidth-intensive operations. Such allocation of duties is exemplary only. In one implementation, the high-speed controller 1208 is coupled to memory 1204, display 1216, e.g., through a graphics processor or accelerator, and to high-speed expansion ports 1210, which may accept various expansion cards (not shown). In the implementation, low-speed controller 1212 is coupled to storage device 1206 and low-speed expansion port 1214. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can process instructions for execution within the computing device 1250, including instructions stored in the memory 1264. The processor may also include separate analog and digital processors. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT LCD display or an OLED display, or other appropriate display technology. The display interface 1256 may include appropriate circuitry for driving the display 1254 to present graphical and other information to a user. The control interface 1258 may receive commands from a user and convert them for submission to the processor 1252. In addition, an external interface 1262 may be provided in communication with processor 1252, so as to enable near area communication of device 1250 with other devices. External interface 1262 may provide, for example, for wired communication, e.g., via a docking procedure, or for wireless communication, e.g., via Bluetooth or other such technologies.

The memory 1264 stores information within the computing device 1250. In one implementation, the memory 1264 is a computer-readable medium. In one implementation, the memory 1264 is a volatile memory unit or units. In another implementation, the memory 1264 is a non-volatile memory unit or units. Expansion memory 1274 may also be provided and connected to device 1250 through expansion interface 1272, which may include, for example, a SIMM card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provided as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, or memory on processor 1252.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS receiver module 1270 may provide additional wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound, e.g., voice messages, music files, etc., and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer device implemented method comprising:
obtaining optical signals reflected through a fiber, the fiber comprising one or more embedded sensors and a nano-magnetometer embedded at a distal location of the fiber;
determining a frequency shift of each of the reflected optical signals, the frequency shift imparted on the reflected optical signals by the one or more embedded sensors;
determining a phase shift of each of the reflected optical signals, the phase shift imparted on the reflected optical signals by the nano-magnetometer; and
determining one or more characteristics of the fiber using the determined frequency shift and the phase shift of each of the reflected optical signals, wherein the one or more characteristics of the fiber comprises a shape of the fiber and a location of the fiber in relation to an external reference.

2. The computer device implemented method of claim 1, wherein determining the one or more characteristics of the fiber comprises determining the location of the fiber using at least the determined phase shift of each of the reflected optical signals.

3. The computer device implemented method of claim 1, wherein determining the one or more characteristics of the fiber comprises determining the shape of the fiber using at least the determined frequency shift of each of the reflected optical signals.

4. The computer device implemented method of claim 1, further comprises instructing a tunable laser to transmit the optical signals through the fiber.

5. The computer device implemented method of claim 4, wherein the optical signals comprise light having a range of wavelengths.

6. The computer device implemented method of claim 1, wherein determining the phase shift of each of the reflected optical signals further comprises:
determining one or more magnetic fields sensed by the nano-magnetometer from the determined phase shift of each of the reflected optical signals; and identifying a location of the nano-magnetometer at the distal location of the fiber using the one or more determined magnetic fields.

7. The computer device implemented method of claim 6, wherein determining the frequency shift of each of the reflected optical signals further comprises determining a measure of bend at various locations along the fiber using the determined frequency shift of each of the reflected optical signals.

8. The computer device implemented method of claim 7, wherein determining the one or more characteristics of the fiber using the determined frequency shift and the determined phase shift of each of the reflected optical signals further comprises:

determining a strain of the fiber using the determined measure of bend at the various locations along the fiber using the determined frequency shift, wherein the determined frequency shift of each of the reflected optical signals represents: (i) a location of the strain of the fiber and (ii) a location of each of the one or more embedded sensors in the fiber;

wherein the one or more characteristics of the fiber comprises (i) a curvature of the fiber at the location of the strain (ii) an angle of the curvature at the location of the strain, (iii) the shape of the fiber, and (iv) the location of the fiber.

9. The computer device implemented method of claim 8, further comprising:

estimating the shape of the fiber by combining, at each location of the strain, the curvature of the fiber and the angle of the curvature; and determining the location of the fiber using (i) the estimated shape of the fiber and (ii) the identified location of the nano-magnetometer, wherein the external reference represents the identified location of the nano-magnetometer.

10. The computer device implemented method of claim 9, wherein the estimated shape of the fiber indicates a shape of the fiber in three-dimensional spatial coordinates, and wherein the estimated shape of the fiber comprises one or more of an orientation of a center of the fiber, a first radial axis of the fiber, and a second radial axis of the fiber.

11. The computer device implemented method of claim 1, wherein the one or more embedded sensors comprise one or more Fiber Bragg Gratings (FBG) embedded at various locations along the fiber.

12. The computer device implemented method of claim 1, wherein the fiber comprises a plurality of cores, wherein the nano-magnetometer reflects a portion of the optical signals through a first subset of the cores of the plurality of the cores and the one or more embedded sensors reflects a portion of the optical signals through a second subset of the cores, wherein the first subset of the cores are different from the second subset of the cores.

13. The computer device implemented method of claim 1, further comprising:

training a machine-learning model to predict the one or more characteristics of the fiber using the determined frequency and the phase shift of each of the reflected optical signals; and applying the trained machine-learning model.

14. The computer device implemented method of claim 1, further comprising:

shifting a wavelength of the nano-magnetometer within an operating range of an interrogator.

15. The computer device implemented method of claim 1, wherein the fiber is positioned in a surgical environment.

16. A system comprising:

one or more computers and one or more storage devices storing instructions that are operable, when executed by the one or more computers, to cause the one or more computers to perform operations comprising:

obtaining optical signals reflected through a fiber, the fiber comprising one or more embedded sensors and a nano-magnetometer embedded at a distal location of the fiber;

determining a frequency shift of each of the reflected optical signals, the frequency shift imparted on the reflected optical signals by the one or more embedded sensors;

determining a phase shift of each of the reflected optical signals, the phase shift imparted on the reflected optical signals by the nano-magnetometer; and determining one or more characteristics of the fiber using the determined frequency shift and the phase shift of each of the reflected optical signals, wherein the one or more characteristics of the fiber comprises a shape of the fiber and a location of the fiber in relation to an external reference.

17. The system of claim 16, wherein determining the one or more characteristics of the fiber comprises determining the location of the fiber using at least the determined phase shift of each of the reflected optical signals.

18. The system of claim 16, wherein determining the one or more characteristics of the fiber comprises determining a shape of the fiber using at least the determined frequency shift of each of the reflected optical signals.

19. The system of claim 16, further comprises instructing a tunable laser to transmit the optical signals through the fiber.

20. The system of claim 19, wherein the optical signals comprise light having a range of wavelengths.

21. The system of claim 16, wherein determining the phase shift of each of the reflected optical signals further comprises:

determining one or more magnetic fields sensed by the nano-magnetometer from the determined phase shift of each of the reflected optical signals; and identifying a location of the nano-magnetometer at the distal location of the fiber using the one or more determined magnetic fields.

22. The system of claim 21, wherein determining the frequency shift of each of the reflected optical signals further comprises determining a measure of bend at various locations along the fiber using the determined frequency shift of each of the reflected optical signals.

23. The system of claim 22, wherein determining the one or more characteristics of the fiber using the determined frequency shift and the determined phase shift of each of the reflected optical signals further comprises:

determining a strain of the fiber using the determined measure of bend at the various locations along the fiber using the determined frequency shift, wherein the determined frequency shift of each of the reflected optical signals represents: (i) a location of the strain of the fiber and (ii) a location of each of the one or more embedded sensors in the fiber, wherein the one or more characteristics of the fiber comprises (i) a curvature of the fiber at the location of the strain (ii) an angle of the curvature at the location of the strain, (iii) the shape of the fiber, and (iv) the location of the fiber.

24. The system of claim 23, further comprising:

estimating the shape of the fiber by combining, at each location of the strain, the curvature of the fiber and the angle of the curvature; and determining the location of the fiber using (i) the estimated shape of the fiber and (ii) the identified location of the nano-magnetometer, wherein the external reference represents the identified location of the nano-magnetometer.

25. The system of claim 24, wherein the estimated shape of the fiber indicates a shape of the fiber in three-dimensional spatial coordinates, and wherein the estimated shape of the fiber comprises one or more of an orientation of a center of the fiber, a first radial axis of the fiber, and a second radial axis of the fiber.

26. The system of claim 16, wherein the one or more embedded sensors comprise one or more Fiber Bragg Gratings (FBG) embedded at various locations along the fiber.

27. The system of claim 16, wherein the fiber comprises a plurality of cores, wherein the nano-magnetometer reflects a portion of the optical signals through a first subset of the cores of the plurality of the cores and the one or more embedded sensors reflects a portion of the optical signals through a second subset of the cores, wherein the first subset of the cores are different from the second subset of the cores.

28. The system of claim 16, further comprising:

training a machine-learning model to predict the one or more characteristics of the fiber using the determined frequency and the phase shift of each of the reflected optical signals; and applying the trained machine-learning model.

29. The system of claim 16, further comprising:

shifting a wavelength of the nano-magnetometer within an operating range of an interrogator.

30. A non-transitory computer-readable medium storing software comprising instructions executable by one or more computers which, upon such execution, cause the one or more computers to perform operations comprising:

obtaining optical signals reflected through a fiber, the fiber comprising one or more embedded sensors and a nano-magnetometer embedded at a distal location of the fiber;

determining a frequency shift of each of the reflected optical signals, the frequency shift imparted on the reflected optical signals by the one or more embedded sensors;

determining a phase shift of each of the reflected optical signals, the phase shift imparted on the reflected optical signals by the nano-magnetometer; and determining one or more characteristics of the fiber using the determined frequency shift and the phase shift of each of the reflected optical signals, wherein the one or more characteristics of the fiber comprises a shape of the fiber and a location of the fiber in relation to an external reference.

* * * * *